United States Patent
Blom-Schieber et al.

(10) Patent No.: US 10,169,492 B2
(45) Date of Patent: Jan. 1, 2019

(54) FIBER PLACEMENT OPTIMIZATION FOR STEERED-FIBER PLIES

(71) Applicant: The Boeing Company, Chicago, IL (US)

(72) Inventors: Adriana Willempje Blom-Schieber, Shoreline, WA (US); Laura Sumi Kang, Seattle, WA (US); Jan Hendrik Vandenbrande, Sammamish, WA (US)

(73) Assignee: The Boeing Company, Chicago, IL (US)

(*) Notice: Subject to any disclaimer, the term of this patent is extended or adjusted under 35 U.S.C. 154(b) by 881 days.

(21) Appl. No.: 14/295,441

(22) Filed: Jun. 4, 2014

(65) Prior Publication Data
US 2014/0288893 A1 Sep. 25, 2014

Related U.S. Application Data

(63) Continuation-in-part of application No. 13/164,701, filed on Jun. 20, 2011, now Pat. No. 8,756,037.

(51) Int. Cl.
*G06F 17/50* (2006.01)
*B29C 70/38* (2006.01)
(Continued)

(52) U.S. Cl.
CPC .......... *G06F 17/50* (2013.01); *G06F 17/5018* (2013.01); *B26D 7/18* (2013.01); *B29C 33/58* (2013.01); *B29C 70/16* (2013.01); *B29C 70/38* (2013.01); *B29C 70/382* (2013.01); *B29C 70/384* (2013.01); *B29C 70/386* (2013.01); *B29C 70/388* (2013.01);
(Continued)

(58) Field of Classification Search
None
See application file for complete search history.

(56) References Cited

U.S. PATENT DOCUMENTS 5,472,553 A * 12/1995 Roberts .................... B26D 7/18
  156/353
5,562,788 A * 10/1996 Kitson .................. B29C 70/384
  156/378

(Continued)

OTHER PUBLICATIONS

A. W. Blom, M. M. Abdalla, Z. Gurdal, "Optimization of course locations in fiber-placed panels for general fiber angle distributions" pp. 564-570, 2010.*

(Continued)

*Primary Examiner* — Kibrom K Gebresilassie
(74) *Attorney, Agent, or Firm* — Ostrager Chong Flaherty & Broitman, P.C.

(57) ABSTRACT

Methods for optimizing fiber placement programming for use in automated manufacture of steered-fiber composite laminates. The optimization methods are implemented in software capable of optimally translating steered-fiber laminate definitions in fiber placement code for manufacturing steered-fiber laminates without overlaps. The optimization is set up to take into account manufacturing constraints, such as minimum cut length, minimum steering radius, and fiber straightening due to steering. This software includes both geometry and optimization and will take the aforementioned issues into account by optimizing the direction of lay down and the location and sequence of cutting and adding individual tows.

21 Claims, 19 Drawing Sheets

(51) Int. Cl.
| | |
|---|---|
| G05B 19/4097 | (2006.01) |
| B29C 70/54 | (2006.01) |
| G06T 7/00 | (2017.01) |
| G01N 21/88 | (2006.01) |
| G05B 19/4099 | (2006.01) |
| B26D 7/18 | (2006.01) |
| B29C 70/16 | (2006.01) |
| B65H 35/00 | (2006.01) |
| B29C 33/58 | (2006.01) |

(52) U.S. Cl.
CPC ........ *B29C 70/545* (2013.01); *B65H 35/0013* (2013.01); *G01N 21/8806* (2013.01); *G05B 19/4097* (2013.01); *G05B 19/4099* (2013.01); *G06F 17/5095* (2013.01); *G06F 2217/08* (2013.01); *G06F 2217/44* (2013.01); *G06T 7/0004* (2013.01)

(56) References Cited

U.S. PATENT DOCUMENTS

| | | | | |
|---|---|---|---|---|
| 6,544,367 | B1* | 4/2003 | Fujimoto | B65H 35/0013 156/187 |
| 6,654,710 | B1 | 11/2003 | Keller | |
| 6,799,081 | B1 | 9/2004 | Hale et al. | |
| 6,959,269 | B1 | 10/2005 | Welterlin | |
| 7,807,002 | B2* | 10/2010 | Engelbart | B29C 70/384 156/350 |
| 7,842,145 | B2* | 11/2010 | Hogg | B29C 70/386 156/160 |
| 7,943,076 | B1* | 5/2011 | Hawkins | B29C 70/30 156/196 |
| 8,318,291 | B2* | 11/2012 | Hogg | B29C 70/386 428/156 |
| 2003/0082315 | A1 | 5/2003 | Mehlman et al. | |
| 2005/0240291 | A1* | 10/2005 | Oldani | B29C 70/382 700/57 |
| 2006/0249868 | A1* | 11/2006 | Brown | B29C 70/342 264/163 |
| 2007/0173966 | A1* | 7/2007 | Oldani | B29C 70/382 700/110 |
| 2007/0280501 | A1* | 12/2007 | Walton | G01N 21/8806 382/100 |
| 2009/0261199 | A1 | 10/2009 | McCarville et al. | |
| 2010/0121625 | A1 | 5/2010 | Krog | |
| 2010/0204815 | A1* | 8/2010 | Murrish | G05B 19/4097 700/98 |
| 2012/0059376 | A1 | 3/2012 | Rains et al. | |
| 2014/0288893 | A1* | 9/2014 | Blom | G06F 17/5018 703/1 |
| 2015/0360440 | A1* | 12/2015 | Kisch | B29C 70/382 428/189 |

OTHER PUBLICATIONS

B. F. Tatting, Z. Gurdal, "Automated Finite Element Analysis of Elastically-Tailored Plates", NASA/CR-2003, 52 pages.*

Blom et al., "Optimization of a composite cylinder under bending by tailoring stiffness properties in circumferential direction," Composites: Part B, vol. 41 (2010), pp. 157-165.

Tatting et al., Automated Finite Element Analysis of Elastically-Tailored Plates, Dec. 2003, pp. 1-52.

Blom et al. "Optimization of Tow-Placed, Tailored Composite Laminates," 16th Int'l Conference on Composite Materials, Kyoto, Japan, Jul. 8-13, 2007.

Liu et al., "A Strength-Based Multiple Cutout Optimization in Composite Plates Using Fixed Grid Finite Element Method," Composite Structures, vol. 73 (2006), pp. 403-412.

Blom et al., "Optimization of Course Locations in Fiber-Placed Panels for General Fiber Angle Distributions;" Composites Science and Technology, vol. 70, No. 4 (2010), pp. 564-570.

Blom, "Structural Performance of Fiber-Placed, Variable-Stiffness Composite Conical and Cylindrical Shells," Ph.D. Thesis, Delft University of Technology, The Netherlands (2010).

Setoodeh et al., "Generating Curvilinear Fiber Paths from Lamination Parameters Distributions", 47th AIAA/ASME/ASCE/AHS/ASC Structures, Structural Dynamics, and Materials Conference, May 1-4, 2006, Newport, Rhode Island, AIAA 2006-1875.

Keller, "Optimization of ply angles in laminated composite structures by a hybrid, asynchronous, parallel evolutionary algorithm", Composite Structures, vol. 92, No. 11, Oct. 1, 2010, pp. 2781-2790.

Julien et al., "Generating realistic laminate fiber angle distributions for optimal variable stiffness laminates". Composites: Part B, vol. 43, No. 2, Mar. 1, 2012, pp. 354-360.

Booker et al., "A Rigorous Framework for Optimization of Expensive Functions by Surrogates," Center for Research on Parallel Computation, Rice University, CRPC-TR98739-S, Feb. 1998.

* cited by examiner

FIBER PLACEMENT OPTIMIZATION FOR STEERED-FIBER PLIES

RELATED PATENT APPLICATION

This application is a continuation-in-part of and claims the benefit of and priority from U.S. patent application Ser. No. 13/164,701 filed on Jun. 20, 2011, which issued as U.S. Pat. No. 8,756,037 on Jun. 17, 2014 and the disclosure of which is incorporated by reference herein in its entirety.

BACKGROUND

The methodology disclosed herein generally relates to systems and methods for producing composite laminates using tow placement technology. In particular, the methodology disclosed herein relates to the automated design of variable-stiffness composites comprising plies with spatially varying fiber orientation.

Fiber-reinforced composite materials comprise fibers embedded in a matrix material, such as thermoset and thermoplastic polymer resins. The fibers carry loads and provide strength and stiffness. A tape layer in a composite material has high strength and stiffness in the direction of the fiber, and lower strength and stiffness in a direction perpendicular to the fiber.

Fiber-reinforced composite laminates are usually constructed of plies with constant fiber orientations. Laminate stiffness is varied on a panel-by-panel basis by dropping and adding plies. A more natural way of varying laminate stiffness is to gradually change the fiber orientation in the plane of individual plies. Steered-fiber laminates provide potential to reduce weight, because they allow in-plane stiffness tailoring, resulting in beneficial load redistribution. For certain applications the stiffness can be varied to tailor load paths such that local load levels near critical areas such as cutouts are reduced, ultimately leading to lighter structures. Production of these laminates is possible using advanced fiber placement technology, which enables the placement of curved fiber courses on a surface.

Advanced fiber placement (also known as "tow placement technology") is a fully automated process for the production of composite laminates that combines the differential payout capability of filament winding and the compaction and cut-restart capabilities of automated tape laying. A variety of machines exist that can deposit different kinds of materials: fiber-reinforced thermoset prepreg (pre-impregnated) materials, fiber-reinforced thermoplastic materials, or dry fibers. Carbon fibers pre-impregnated with thermoset resin are most commonly used in the aerospace industry and therefore the fiber placement process will be described herein assuming a thermoset material system.

Most fiber placement systems have seven axes of motion and are computer controlled. The axes of motion, i.e., three position axes, three rotation axes and an axis to rotate the work mandrel, provide the fiber placement machine flexibility to position the fiber placement head onto the part surface, enabling the production of complicated composite parts. During the fiber placement process, tows of slit prepreg tape are placed on the surface in bands of parallel fibers, called courses (i.e., each course consists of multiple parallel tows). Typical tow widths are 3.175, 6.35, and 12.7 mm (⅛, ¼, and ½ inch). This technique allows fibers to be curved and tows to be cut and restarted individually, making it possible to manufacture parts that are close to their final shape, thus reducing scrap rates. The tow cut and restart capability of fiber placement machines also enables variation of the course width, which can be used to eliminate gaps or overlaps between neighboring courses that are caused by geometry and steered fiber courses.

Advanced fiber placement has substantially increased the capabilities for manufacturing composite laminates, but it also has a number of limitations, which are more important for steered-fiber laminates than for non-steered-fiber laminates. In steered-fiber laminates courses are not parallel to each other, causing courses to overlap each other if the course width is kept constant, assuming no gaps between courses is allowed. Tows can be cut and restarted if overlaps are undesired. The exact position of these tow cuts/restarts with respect to the boundary of a neighboring course or a ply boundary is determined by the coverage parameter. Tows are cut perpendicular to the fiber direction, causing a non-smooth course boundary and small triangular overlaps or gaps. More tow cutting/restarting is needed for steered-fiber laminates than for non-steered-fiber laminates, increasing the influence of these small triangular overlaps and gaps on the laminate quality. Therefore the coverage parameter is more important for steered-fiber laminates. The amount of tow cutting/restarting that is necessary to achieve a "near-constant" thickness can be quantified by the amount of thickness build-up that would occur if no tows would be cut at all, i.e., if the course width was kept constant. Thickness build-up depends on the surface geometry and the amount of fiber steering used to tailor laminate stiffness, but is typically more pronounced in steered-fiber laminates. A physical restriction of fiber placement machines is the minimum length of a tow that can be placed, called the "minimum cut length". Short tows in non-steered laminates typically occur at ply boundaries, where they are either extended beyond the minimum cut length, or left out. In steered-fiber laminates short tows can occur in the middle of a ply, where extending or leaving out the tow is undesirable, because they create flaws in the laminate. Other effects directly related to fiber steering are tow puckering, folded tows, and straightening of curved tows when they are cut. These effects are more pronounced for smaller in-plane turning radii. A minimum turning radius is defined to ensure laminate quality is not significantly affected by tow puckering or folded tows. Tow straightening depends on lay-down direction and turning radius. Finally, plies in non-steered laminates are usually programmed based on one reference direction and offsets to that curve, or on a small number of guide curves in-between which interpolation is used to define the course centerlines. Steered-fiber laminates require a large number of guide curves to ensure that the as-manufactured fiber orientations match the as-designed fiber orientations. The fiber placement definition, which includes centerline locations, tow cut/restart locations and laydown direction, can be optimized to avoid or minimize the effects of fiber steering and tow cutting/restarting while ensuring the desired fiber orientations are achieved.

There is a need for software capable of optimally translating steered-fiber laminate ply definitions in fiber placement code for manufacturing steered-fiber laminates, taking into account all manufacturing constraints, especially ones that are specific to steered-fiber plies, such as minimum cut length occurring within a ply instead of at the boundary, fiber straightening, and long gaps that might occur when courses go parallel.

SUMMARY

The subject matter disclosed herein includes methods for optimizing fiber placement programming for use in automated manufacture of steered-fiber composite laminates. The optimization methods are implemented in software that translates steered-fiber laminate definitions in fiber placement code for manufacturing steered-fiber laminates. The optimization is set up to take into account manufacturing constraints, such as minimum cut length and fiber straightening due to steering. This software includes both geometry and course optimization and will take the aforementioned issues into account by optimizing the direction of lay down and the location and sequence of cutting and adding individual tows. The optimization approach disclosed herein can easily be extended to traditional and steered plies on three-dimensional geometries.

One aspect of the subject matter disclosed in detail below is a method, performed by a computer system, for determining tow cut locations for steered-fiber placement. The method comprises: (a) generating stream function data with a multiplicity of corresponding stream lines; (b) generating course pair data representing successive pairs of neighboring courses having centerlines corresponding to the stream lines representing the stream function data generated in operation (a) such that there is no gap between the courses and the overlap is minimized (no-gap-minimum-overlap condition); and for each pair of neighboring courses: (c) determining potential tow cut locations in areas of overlap between courses and splitting up individual tows at these locations creating tow segments; (d) generating a list of data for each tow that indicates the potential tow cut locations along its length, a list of parameters representing the tow segments, a list of data specifying the lengths of the tow segments, and two lists of data specifying the centerline curvatures at the minimum cut length distance from each potential tow cut location at either side of the potential tow cut location; and (e) selecting which tows of the pair of neighboring courses should be cut (or added) and at which potential tow cut locations, i.e., which of the tow segments are placed on the surface and which are not, and in which direction the course should be laid down, taking a plurality of constraints into account (such as a maximum thickness build-up, a minimum turning radius, a coverage parameter, a minimum cut length, and a maximum number of cuts within an overlap area); and (f) generating machine code for controlling a fiber placement machine to cut tows and lay down courses in accordance with selections made in operation (e). The method may further comprise displaying a visual representation of a steered-fiber ply comprising a multiplicity of courses, each course comprising a respective multiplicity of tows, including tows selected for cutting in operation (e) with overlaps that conform to a coverage parameter constraint. Operation (e) may comprise finding a set of tow cuts which minimize a penalty function for one set of courses, generating a list of segment variables for each tow, indicating whether it is active or inactive, and generating a list of cut variables, indicating whether a tow is cut or added at a potential tow cut location or if the status is unchanged. Finding the optimum tow cut location will generate the list that indicates which tow segments should be placed or left out, which then defines where tows are cut/started.

The penalty function is used to enforce the various constraints and desirable features. Each constraint or feature can be assigned a different weighing factor to indicate relative importance, because it is unlikely that all constraints can be satisfied. Physical constraints, such as the minimum cut length and overlap between tows will have a large weighing factor compared to desirable features such as a certain coverage factor, gap area or fiber straightening due to cutting tows at a small radius. The mathematical implementation includes an overlap constraint, according to which only one tow segment can be active when there is an overlap, a non-overlap constraint, according to which a tow segment is active when there is no overlap, and a minimum cut length. In addition, operation (e) takes the following constraints into account: (1) none of the tows between the two outermost tows that are not cut should be cut; and (2) if a curvature of a path of a course is larger than a specified threshold, the tows along an outer radius of the course are not cut to avoid fiber straightening (depending on the direction in which the course is laid down). One could also optimize the direction and sequence in which courses are laid down.

In the method described above, operation (b) may further comprise the following steps performed when one course of a pair of neighboring courses completely exits and then re-enters a specified ply domain: replacing the re-entering course by multiple courses by splitting up the re-entering course at the domain boundary; for each newly created course: determining the overlap between the new course and the neighboring course; adjusting the position of the new course to reduce the amount of overlap below a certain threshold if the amount of overlap is larger than this threshold, for example by following the no-gap-minimum-overlap rule; generating course data for the newly created courses and original neighboring course.

In the method described above, the course generation in step (b) might be adjusted if the outcome of step (e) is not satisfactory, i.e., if there is no feasible solution, for example due to a short tow segment violating the minimum cut length, and steps (c) through (e) might be repeated until the outcome of step (e) is satisfactory.

The method described above may further comprise: storing the machine code generated in operation (f) on a computer-readable medium, and operating a computer numerical control tow placement machine in accordance with the machine code stored on the computer-readable medium.

Another aspect is a method for laying a composite ply comprising steered fibers, comprising: (a) generating stream function data with a multiplicity of corresponding stream lines; (b) generating course pair data representing successive pairs of neighboring courses having centerlines corresponding to the stream lines representing the stream function data generated in operation (a) such that there is no gap between the courses and the overlap is minimized; and for each pair of neighboring courses: (c) determining potential tow cut locations in areas of overlap between courses and splitting up individual tows at these locations to create tow segments, (d) generating geometry data for each potential tow cut location, and (e) minimizing a value of a penalty function for simulated placement of tows for one set of courses, taking into account a plurality of constraints; (f) generating machine code for controlling a fiber placement machine to cut tows and lay down courses in accordance with the results of operation (e); and (g) automatically laying down courses and cutting tows in accordance with the machine code, wherein steps (a) through (f) are performed by processors.

A further aspect is a system for designing a steered-fiber ply, comprising one or more processors programmed to execute the following operations: (a) generating stream function data with a multiplicity of corresponding stream lines; (b) generating course pair data representing successive pairs of neighboring courses having centerlines corresponding to the stream lines representing the stream function data generated in operation (a) such that there is no gap between the courses and the overlap is minimized; and for each pair of neighboring courses: (c) determining potential tow cut locations in areas of overlap between courses and splitting up individual tows at these locations to create tow segments, (d) generating geometry data for each potential tow cut location, and (e) minimizing a value of a penalty function for simulated placement of tows for one set of courses, taking into account a plurality of constraints; and (f) generating machine code for controlling a fiber placement machine to cut tows and lay down courses in accordance with the results of operation (e).

The system may further comprise a display device, wherein one of the processors is programmed to control the display device to display a visual representation of a steered-fiber ply comprising a multiplicity of courses, each course comprising a respective multiplicity of tows, including tows selected for cutting in operation (e) with overlaps that conform to a coverage parameter constraint.

The benefits of the fiber placement optimization techniques disclosed herein are manifold. The software can start from a stream function definition that defines the steered-fiber plies on a global level. Course centerlines are created based on the stream function, resulting in an accurate representation of the fiber orientation field. Since the optimization algorithm does not rely on the geometry of the problem, it can be easily extended to three-dimensional problems provided that all inputs can be calculated. By allowing users to specify preference by setting a penalty function for soft constraints, this optimization program provides much flexibility for users, who should be able to easily modify the program based on specific problems. User-specified hard constraints can be easily added to the problem. Solving each problem (a pair of neighboring courses) takes less than a second. Overall computational time is very low.

Other aspects of methods for optimizing the fiber placement programming of steered-fiber composite laminates are disclosed below.

BRIEF DESCRIPTION OF THE DRAWINGS

Reference will hereinafter be made to the drawings in which similar elements in different drawings bear the same reference numerals.

DETAILED DESCRIPTION

The laminate design process disclosed herein allows steering the load within a laminate by steering fibers in the plane of individual plies in the laminate. A challenge to designing laminates with steered fibers is effectively describing manufacturable fiber paths. On a high level, steered-fiber plies can be defined by stream functions. The stream functions are the starting point for generating the detailed fiber-placement definition. In accordance with the design optimization process disclosed in U.S. patent application Ser. No. 13/164,701, the stream function is chosen (i.e., parameterized) directly, and then the angle distribution is calculated from the stream function.

The computational optimization process disclosed in U.S. patent application Ser. No. 13/164,701 uses the variable stiffness performance of a steered-fiber composite laminate to guide the design of stream functions describing the fibers to build it. This design process combines a finite element-based analysis tool, appropriate failure criteria and geometry optimization to determine steered angles associated with stream functions by an optimization program to meet target performance requirements, e.g., load condition(s), and failure criteria for a quasi-static or dynamic event. The design process further allows the designer to impose high-level manufacturing constraints, such as maximum in-plane path curvature or thickness build-up within a ply. An optimum solution is attributed to favorable stress or strain distributions for a given loaded structure with steered fibers. Fibers in a steered-fiber panel are typically placed in strips called tows, with multiple tows being laid down side by side to form a course. The stream lines determined by the analytic process are used as target paths for fiber placement (i.e., the fiber placement machine will be programmed to lay the courses such that their centerlines correspond to the stream lines).

Steered fibers take curved paths in the ply, and those paths must be described somehow. A great variety of fiber paths is possible, but they must also follow certain rules to be manufacturable: (1) paths must not curve too much (too small steering radii cause wrinkles); and (2) paths must not converge too much (thickness build-up or tow cuts/adds result).

Figure 1:
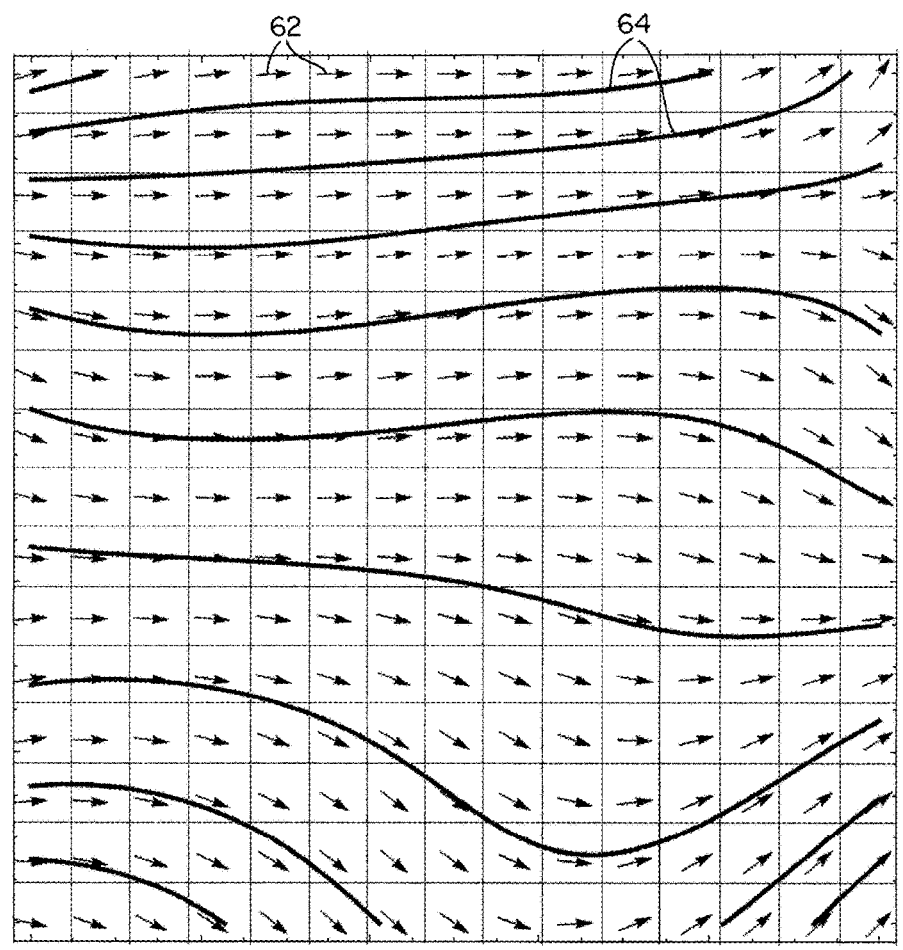
FIG. 1 is a diagram representing a direction field (i.e., fiber orientation variation) of a steered-fiber ply.

Each discrete course path can be described separately, but in design a steered-fiber ply is typically treated as a direction field. FIG. 1 is a diagram showing a direction field (i.e., fiber orientation variation) of a steered-fiber ply. The arrows 62 in FIG. 1 represent the direction field (each arrow shows the direction of a fiber going through that point). The solid lines 64 represent fiber paths. Each fiber path extends from one end of a respective course to the other end. Mathematically, the direction field of a steered-fiber ply can be described as a vector-valued function in the plane of the ply. Fiber direction fields can also be described by the local angle a fiber makes with a ply axis. This leads to a scalar-valued function.

In the design process disclosed in U.S. patent application Ser. No. 13/164,701, the design variables directly define the stream function. With the stream function defined, the thickness distribution and fiber angle distribution are easily computed from the stream function. The stream function itself can be parameterized straightforwardly, for example, by tensor product polynomial splines.

In the final design, the stream lines represent fiber paths. As used herein, a "fiber path" follows the centerline of a finite-width course. Thickness build-up occurs where the stream lines get closer together and consequently courses overlap. Path curvature can be described mathematically as the derivative of the direction field. Thickness build-up can be described mathematically as a function of the gradient of the stream function. One advantage of using the stream function representation of fiber paths for design is that both thickness build-up and steering radius, which are related to derivatives of the stream function, can be controlled more directly.

The design process disclosed in U.S. patent application Ser. No. 13/164,701 enables a more complex (and robust) path description that allows control over various manufacturability constraints. Whatever the path description, most approaches to designing steered-fiber plies rely on optimization techniques to cope with a large design space of steered paths. The process disclosed in U.S. patent application Ser. No. 13/164,701 offers an extended design space while ensuring manufacturability, which is a necessity for practical design.

Another design challenge involves structural analysis methods. Structures may not be designed without a method of predicting their strength (and structural efficiency depends on accuracy of the method). There is a need for analysis methods applicable to slit tape. In particular, work is required for production application of steered fibers, for example, to deal with tow cuts and additions mid-ply and effects of fiber curvature.

Figure 2:
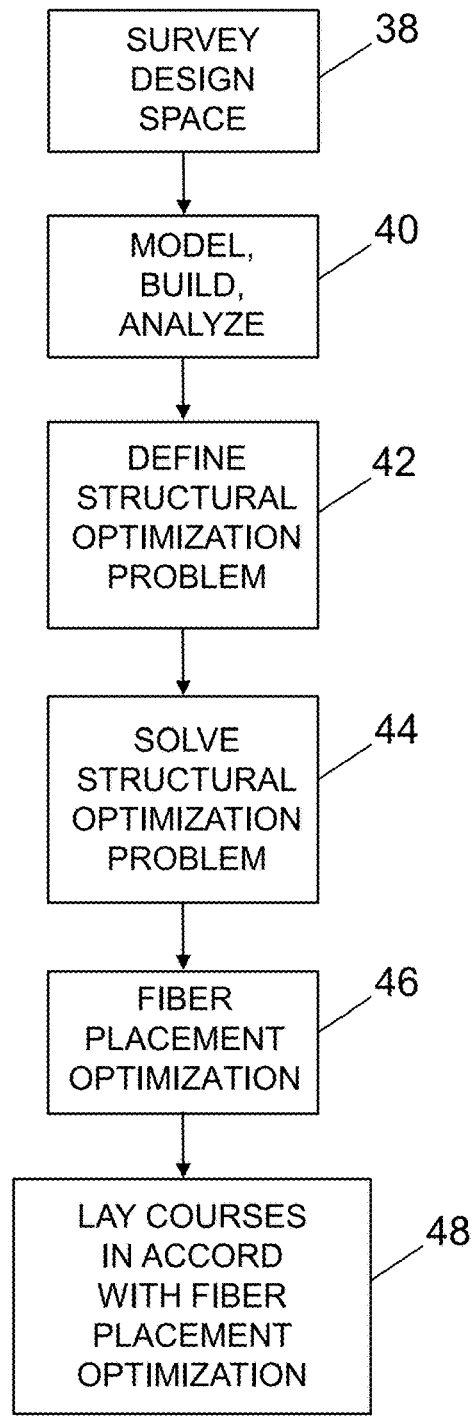
FIG. 2 is a flowchart representing some steps of a process for producing a steered-fiber ply designed in accordance with the process disclosed herein.

FIG. 2 is a flowchart representing the major steps of an optimization process in accordance with one embodiment. The design space is surveyed (step 38) by the optimization program. An experiment is designed to gather response data on the design space for an initial approximate model. This includes defining the domain (specification of input parameters, output responses and bounds on the parameters) and defining the experiment (definition of an experiment based on a Design of Experiments that gives statistical data concerning the samples that will yield the maximum information). Then surrogate models are built, which will allow the optimization algorithm to make inferences about the merits of various structures in the design space (step 40). Thereafter the structural optimization problem is defined (step 42). Then the structural optimization problem is solved (step 44) using an algorithm that uses the approximate models to judiciously choose points at which to run the finite element analysis program, and periodically uses the results of these finite element analyses to improve the approximate model. This process is iterated until completion of the structural optimization, i.e., this process is terminated when computed stream functions are determined that qualify as an optimum design for the steered-fiber plies to be produced. Based on these optimum stream functions, a fiber placement optimization algorithm is performed (step 46). The optimized fiber placements are then converted into a computer program for controlling a multi-axis computer numerical control tow placement machine. When this program is executed to add a steered-fiber ply during lay-up of a composite laminate, respective courses are precisely placed (i.e., laid) with their centerlines disposed along lines corresponding to the stream lines of the optimum stream function (step 48). This is done using a robotic tow placement head, the structure of which is well known in the art. The tows within a course are cut at the end of each traverse and the head is reset for the next run.

Figure 3:
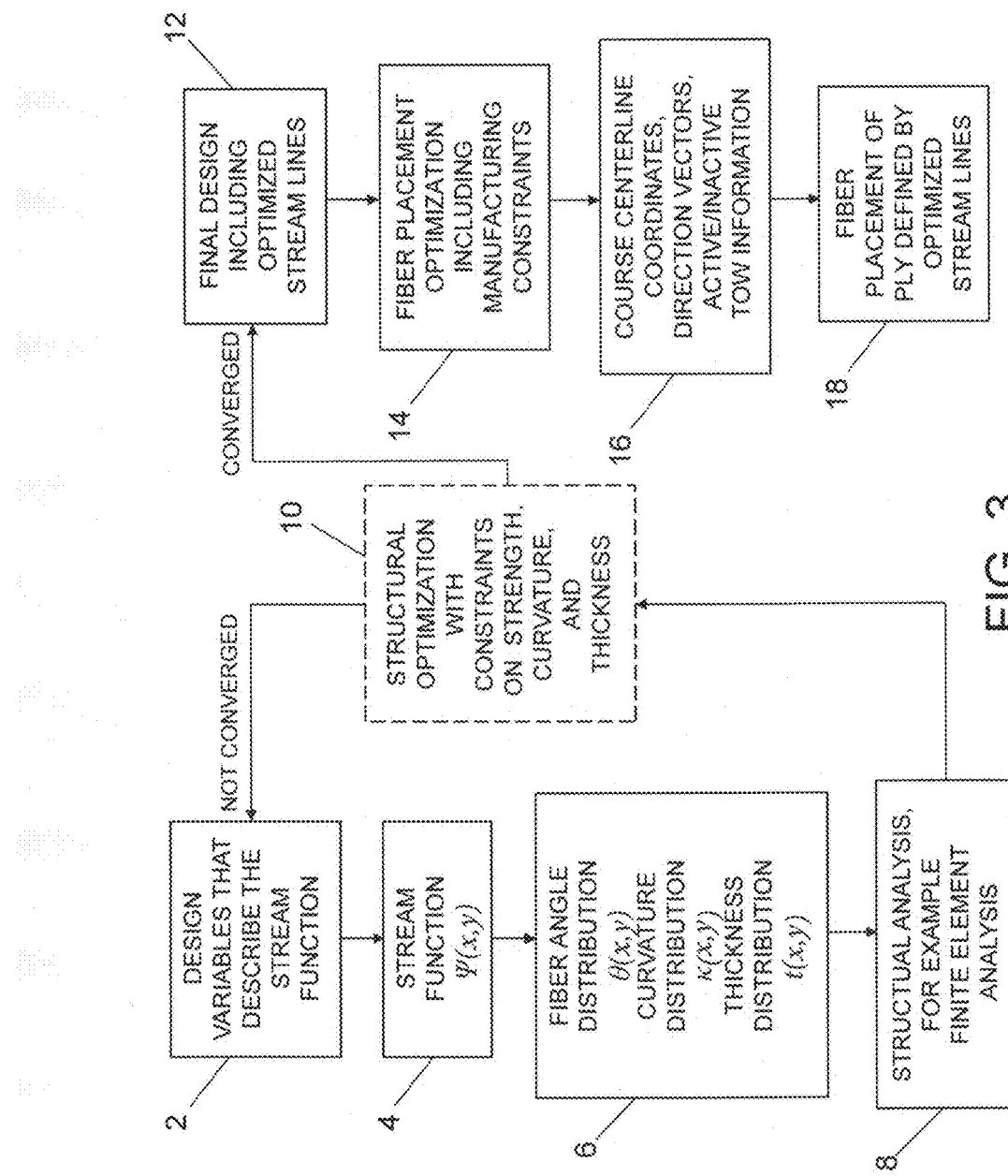
FIG. 3 is a flowchart showing an outline of the analysis process disclosed in detail herein.

FIG. 3 is a flowchart detailing a design process wherein steered-fiber plies are parameterized using stream functions. First, design variable values are selected which directly define the stream function (step 2). Here the stream function is directly defined by the design variables, without having to perform any integration. The stream function can be computed (step 4) using, for example, tensor product polynomial splines. Subsequently, analytical expressions for the fiber angle distribution, curvature distribution and thickness distribution can be derived (step 6). Steps 4 and 6 are performed by a computer programmed to process parametric geometry. The structure simulated with the results of the foregoing computing steps is then analyzed in step 8 by a finite element analysis program for each iteration of the optimization loop. As part of a structural optimization process 10, a measure of merit is computed for the simulated structure using a subroutine that plugs into the finite element analysis program.

The foregoing steps are iterated until the iterative process converges to a best value of a measure of merit (e.g., mass, coefficient of thermal expansion, buckling load, etc.) such that feasibility of the final solution can be guaranteed. In the absence of convergence, the process returns to step 2, in which new design variable values are chosen as a function of the results of the measure of merit computations. The iterative process continues until convergence results in a final (i.e., optimal) design 12, including optimized stream lines. Some manufacturing constraints are applied during the structural optimization 10, meaning that the future choices of design variable values are influenced by whether or not the measures of merit are acceptable for a given design incorporating those constraints. The resulting optimal final design 12, which describes the ply as a continuous angle distribution, cannot be taken directly to a fiber placement machine. In a separate phase of design, the angle distribution is discretized for manufacturing. A fiber placement optimization 14 is performed which includes manufacturing constraints such as minimum cut length and fiber straightening. Programming of the fiber placement machine to lay down individual courses can be optimized for laminate quality and lay-down time. The result of the fiber placement optimization 14 comprises course centerline coordinates, direction vectors, and active/inactive tow information 16. This information can be converted into a program to be executed by a controller of a computer numerical control tow placement machine. The controller is programmed to cause the tow placement machine to lay fibers along paths defined by the optimized stream lines (step 18 in FIG. 3).

The structural optimization 10 takes only minimum turning radius and maximum thickness build-up into account. The fiber placement optimization 14 starts with the optimized stream lines and produces path centerlines, which tows are to be laid down and what direction to lay down the courses. This phase takes into account the rest of the manufacturing constraints, since minimum turning radius and maximum thickness build-up cannot be changed anymore after the stream function is fixed. The aforementioned manufacturing constraints will now be described in more detail.

A. Minimum Turning Radius

When a fiber course is steered, the individual tows are bent in the plane of the surface causing the fibers at the inner radius of the tow to be in compression. These fibers might start buckling out-of-plane if the turning radius is too small. The presence of buckled tows could lead to a reduction in laminate quality. Therefore a limit on the turning radius is imposed, usually defined in terms of a minimum radius for the centerline of the course. Smaller radii are possible, depending on the material system, layup rate, and compaction pressure used. Increasing the tow width increases the amount of compression of the fibers on the inside of the curve, requiring a larger turning radius for courses with larger tow widths. The minimum turning radius constraint is often referred to as the curvature constraint, where the maximum curvature is the inverse of the minimum turning radius allowed.

B. Maximum Thickness Build-Up

Tows can be cut and restarted individually, making it possible to manufacture parts that are close to their final shape, thus reducing scrap rates. The tow cut and restart capability of fiber placement machines also enables variation of the course width, which can be used to eliminate gaps or overlaps between neighboring courses that are caused by geometry and steered-fiber courses. For example, courses laid down in the axial direction on a conical shell would start overlapping at the small radius if the course width is kept constant. A constant-thickness ply can be obtained by cutting (or dropping) tows on the outside of the course when going from the large radius to the small radius. Steered courses can cause overlaps even if the part geometry does not play a role. In general, course edges of two steered courses will not match, unless the courses are exactly parallel, and either gaps or overlaps are formed. Gaps can be avoided by reducing the distance between the course centerlines, while overlaps can be eliminated by cutting and restarting tows.

Figure 4:
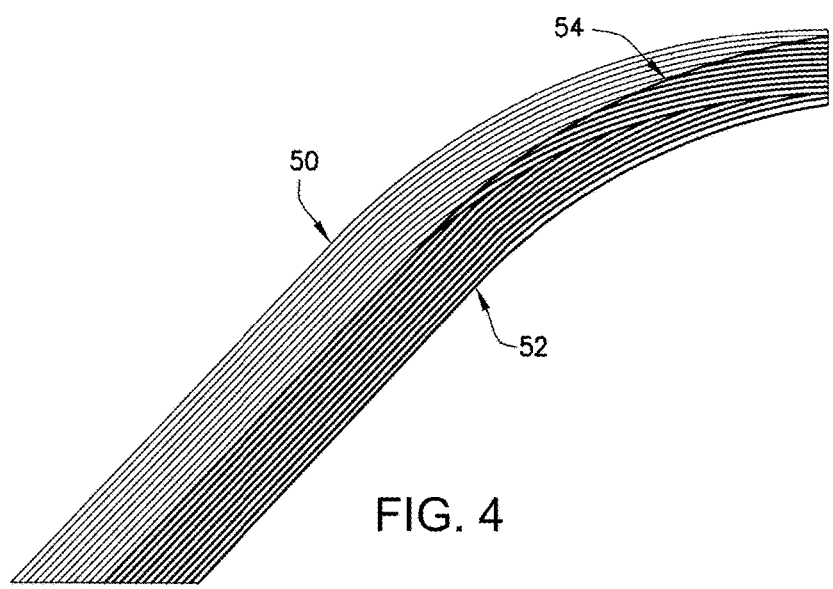
FIG. 4 is a diagram representing convergent courses which overlap.
Figure 5:
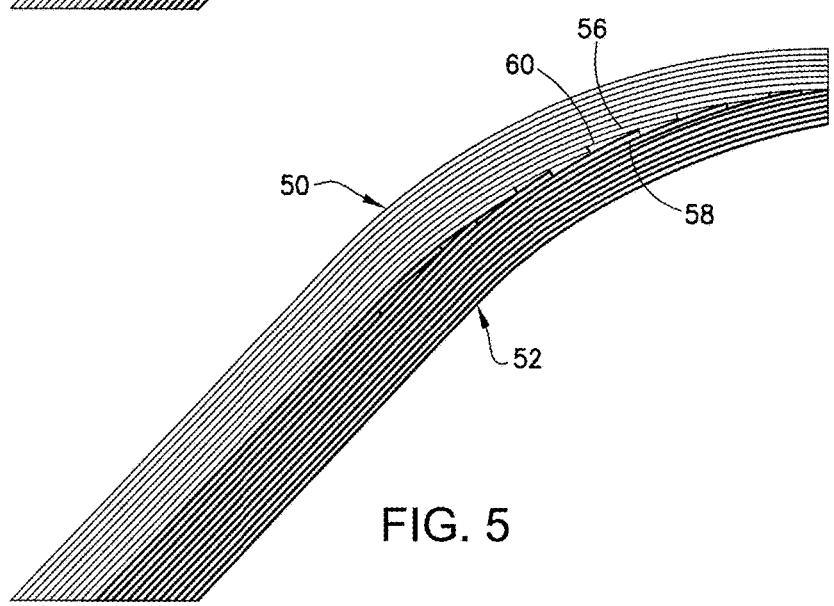
FIG. 5 is a diagram representing convergent courses with tows that have been cut to leave wedge-shaped gaps in the lay-up.

FIG. 4 shows a pair of courses 50 and 52 which converge to produce an area of overlap 54. The overlap will cause thickness to build up unless tows are cut for relief. FIG. 5 shows a pair of courses 50 and 52 having tows 56 and 58 respectively, which have been cut, leaving wedge-shaped gaps 60 in the lay-up. Build-up and cut-gaps can both be reduced by limiting course convergence, i.e., the thickness build-up, within a steered ply during the structural optimization.

The tow cut and restart capabilities of an advanced fiber placement machine can be used to avoid overlaps and create a near-constant-thickness ply, but the effect of converging courses can only be mitigated up to a certain point. Too many rapidly converging courses would require too much tow cutting or even the termination of complete courses, which is impractical for manufacturing and undesirable from a laminate quality perspective. The method used to judge if too much tow cutting is required is to look at the amount of thickness build-up (or overlap) that would be created if the course width were kept constant. For example, five courses, each with thirty tows, converge such that they are on top of each other, causing a thickness build-up of five times the nominal ply thickness. The thickness build-up could be avoided if the width of each course was only one-fifth of the original width, i.e., six tows instead of thirty, because five courses of six tows result in exactly one course width of thirty tows. In other words: the course width is inversely proportional to the amount of thickness build-up. Thus the course width, which is an integer multiple of the tow width, can become too small if the amount of thickness build-up is too large and therefore the amount of thickness build-up has to be constrained.

C. Coverage Parameter

Figure 6A:
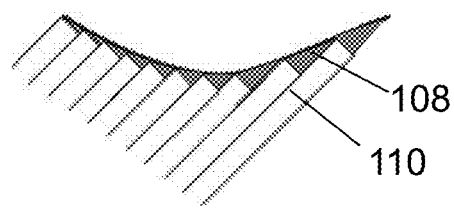
FIGS. 6A through 6C are diagrams representing tow dropping for different coverage parameters: 0% coverage (FIG. 6A); 50% coverage (FIG. 6B); and 100% coverage (FIG. 6C).
Figure 6B:
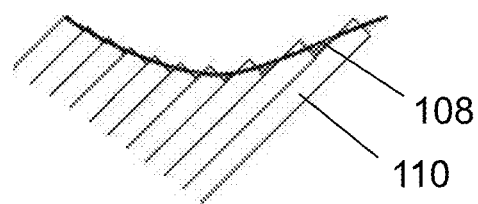
Figure 6C:
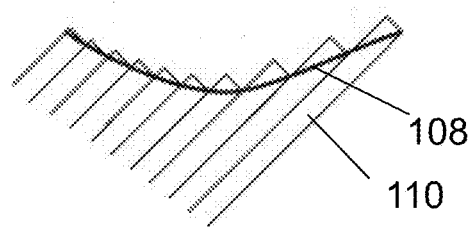

As depicted in FIGS. 6A through 6C, the coverage parameter determines where tows 110 are terminated and restarted with respect to a boundary 108 of a neighboring course or with respect to a ply boundary. Cutting and restarting tows 110 creates either small triangular gaps (shown in FIG. 6A) or small overlaps (shown in FIG. 6B) or a combination of gaps and overlaps (shown in FIG. 6C). A coverage of 0 percent indicates that a tow is cut as soon as one edge reaches the boundary of the neighboring course. This results in a small triangular area without fibers, indicated by shading in FIG. 6A. At 100 percent coverage the tow is cut only when the second tow edge crosses the boundary, creating a small triangular overlap area, as seen in FIG. 6C. Coverage values between 0 and 100 percent represent the intermediate cases. A coverage parameter of 0 percent has been demonstrated to be undesirable because the resin-rich tow-drop areas act as stress raisers, while 100 percent coverage might result in an uneven surface.

D. Minimum Cut Length and Fiber Straightening

The ability of the fiber placement machine to cut and restart tows is used to eliminate overlaps between neighboring courses and to create constant-thickness plies. Sometimes the curved courses require the start and termination of a tow within a course, so the minimum cut length should be taken into account. The minimum cut length is the minimum tow length that needs to be laid down before a tow can be cut after it has been started.

Figure 7:
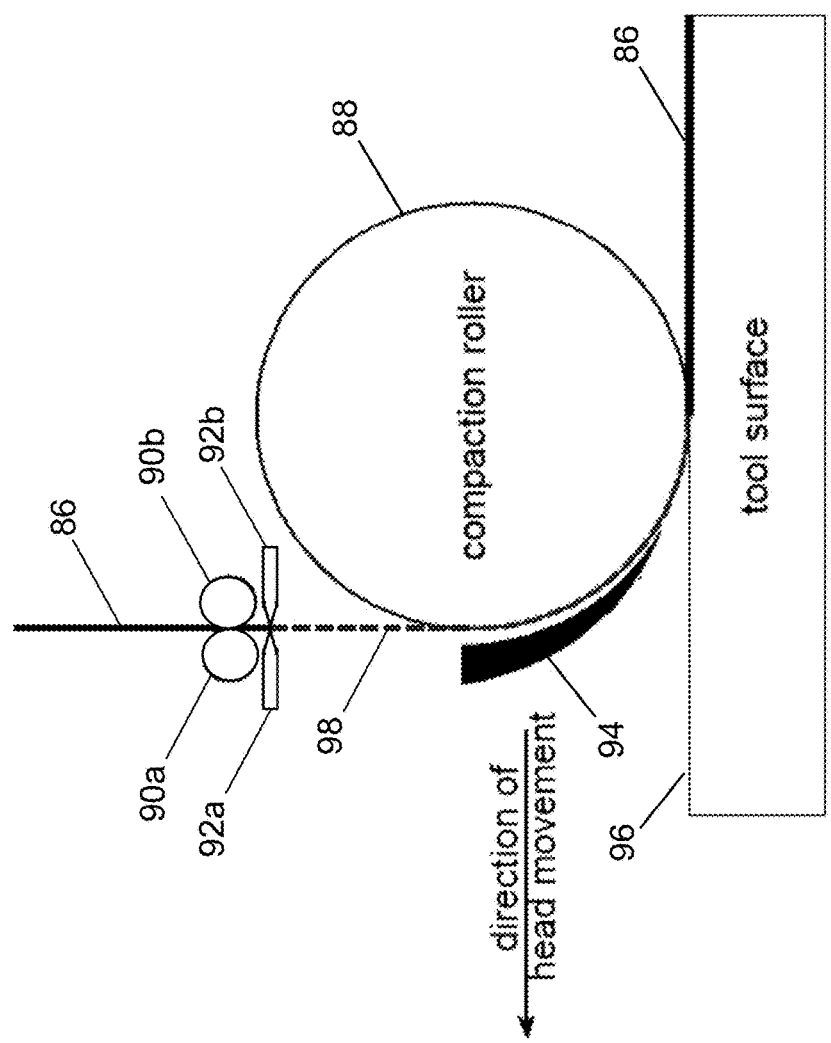
FIG. 7 is a diagram representing a side view of a fiber placement head.

FIG. 7 is a diagram representing a side view of a fiber placement head for placing a course 86 comprising a multiplicity of tows. The tows in course 86 are moved forward by pinching rollers 90a and 90b and guided by a guide 94 toward a nip formed by a compaction (i.e., compression) roller 88 and a tool (e.g., mandrel) surface 96. When a tow of course 86 is restarted, it is moved forward by pinching rollers 90a and 90b until it reaches the nip and is being pulled forward by the friction between the compaction roller 88 and the tool surface 96. If the desired length of the restarted tow to be put down is smaller than the distance between the cutters 92a and 92b and the nip, there is no control over the restarted tow and thus the software prevents the placement of the tow. The minimum cut length is indicated by the dashed line in FIG. 7, which dashed line extends from the cutters 92a and 92b to the nip formed by compaction roller 88 and tool surface 86 and wraps around a portion of the circumferential surface of the compaction roller 88.

Figure 8:
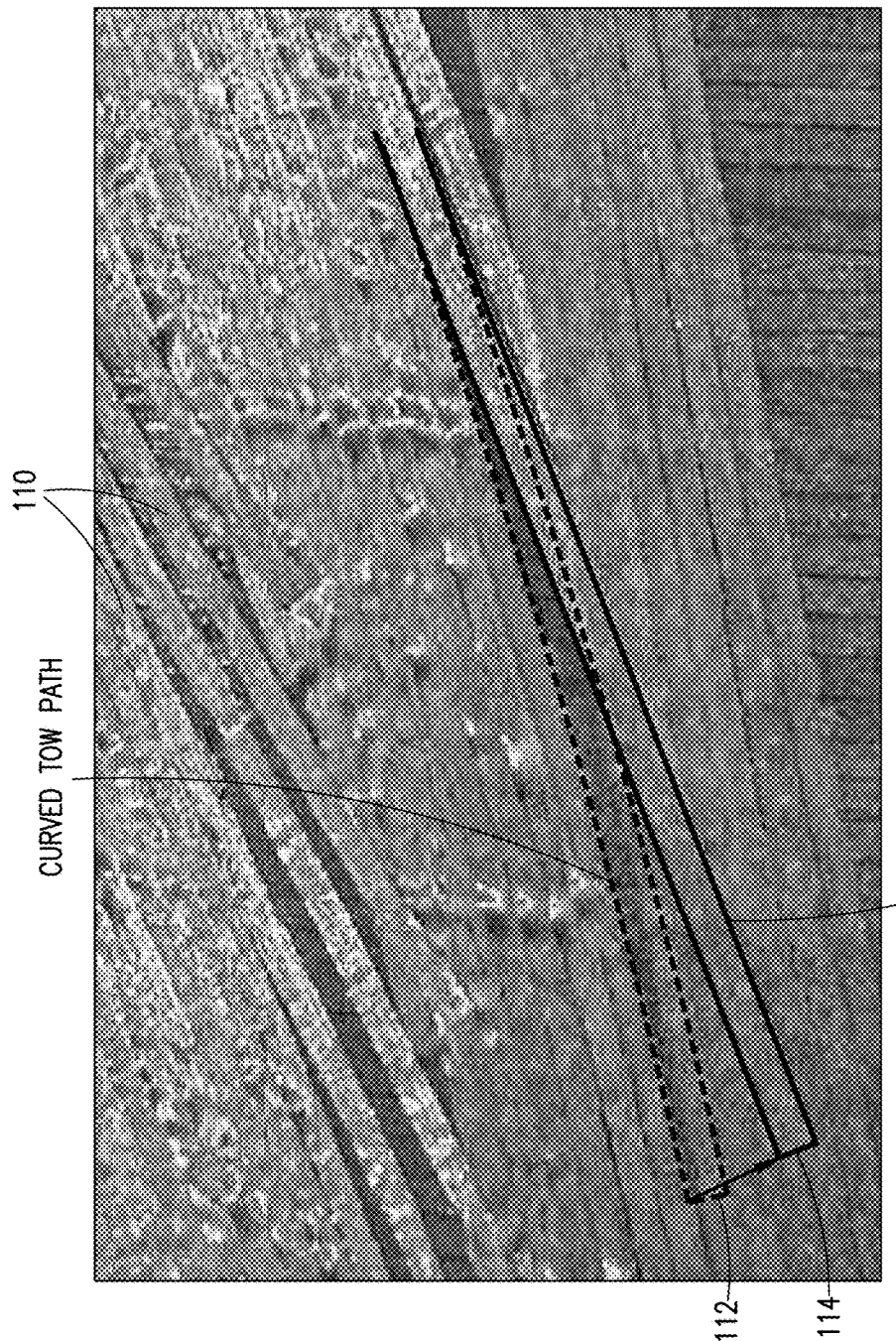
FIG. 8 is a photograph with a graphical overlay showing straightening of a cut tow (indicated by solid lines) that was intended to follow a curved path (indicated by dashed lines).

The minimum cut length also plays a role when a steered fiber path is being placed on the tool surface 86 and tows are cut on the outside of the turn. FIG. 8 is a photograph showing multiple tows 110, with a graphical overlay showing straightening of a cut tow (the straight path 114 being indicated by solid lines) that was intended to follow a curved path 112 (indicated by dashed lines). Once the tow is cut, there is very little control over the direction by the guide anymore and the tow follows the geodesic path 114 instead of the curved path 112, which is referred to herein as "fiber straightening". This is not the case when the tow is cut on the inside of the turn, because then the neighboring tow forces the cut tow to follow the curve. The length over which the tow path deviates from the designed path was measured on a manufactured variable-stiffness cylinder and is equal to the minimum cut length. Fiber straightening can be avoided by designing the steered courses such that no tows are cut on the outside of a turn. Also the deviation from the intended path will be smaller when a larger turn radius is used.

Fiber steering causes some problems when tows are started, more severe when the machine moves slowly: all tows are fed to the surface at the same speed. When steering, the tows have to move faster on the outside of the turn and slower at the inside of the turn. The inner tows might thus be supplied faster than needed, causing the tow to 'bunch up'. The faster the head moves, the smaller the difference between the centerline speed and the inner/outer tow speeds is, and the less of a problem. Overall the problem of starting tows while steering is much smaller than when the tows are cut.

Changing the programming to manipulate where tows are cut and started can result in better quality laminates and require less rework. For example, cutting can be delayed until the radius is large enough that the difference between the curved tow and the geodesic tow is acceptable. In the optimization process disclosed herein, this is implemented as a "penalty" on the measure of merit. In the alternative, cutting tows on the outside of the turn could have higher cost than cutting on the inside of the turn. One method to avoid tow cuts on the outside of a turn is to reverse the direction of lay down. Reversing the direction of lay down converts tow-drops into tow-adds, which solves the fiber straightening problem, because adding tows on the outside of a turn is not a problem. Optimization could take into account the direction of lay down (starting tows is better than cutting), or the fact that the machine has to slow down to cut/add tows.

Figure 9:
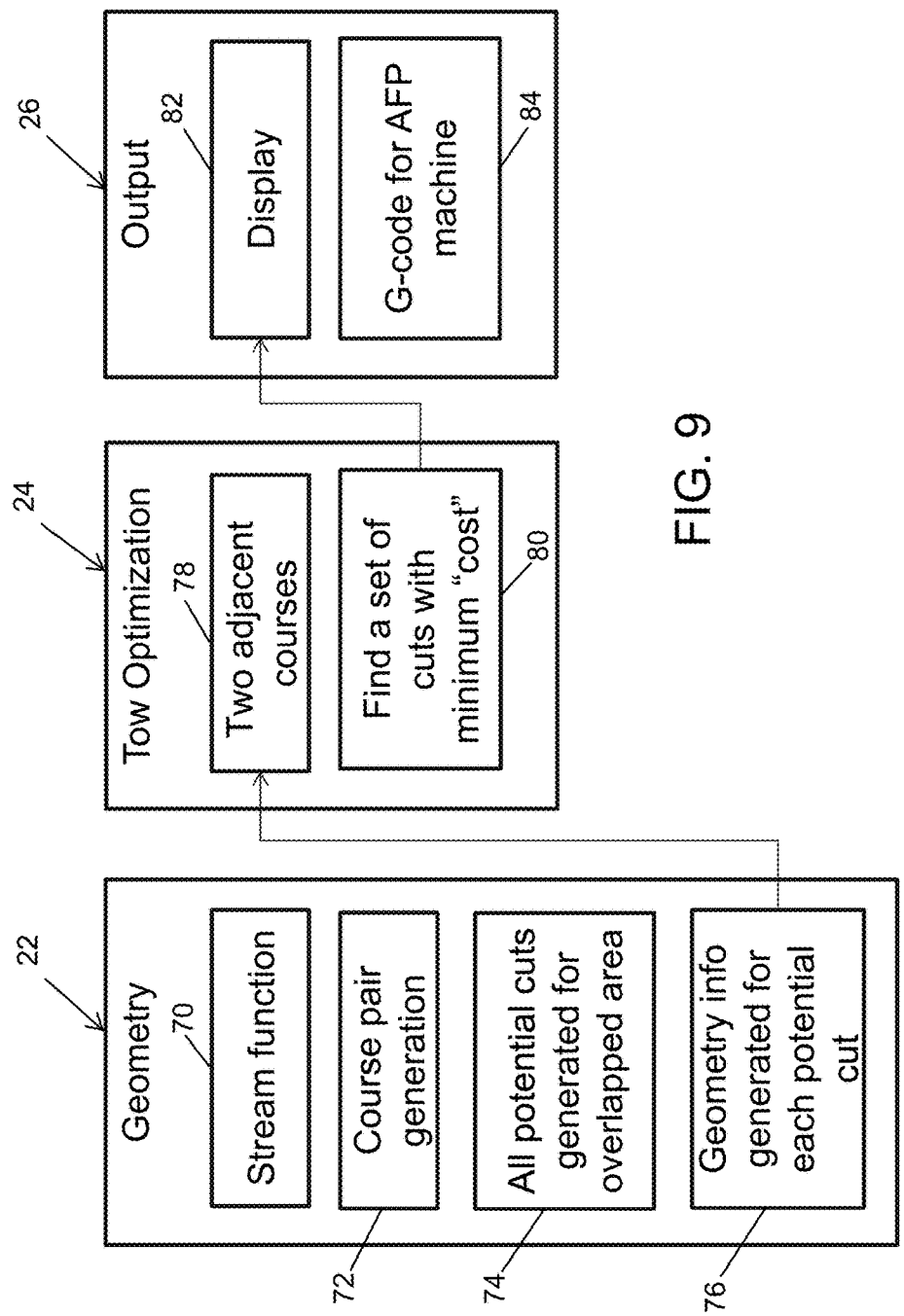
FIG. 9 is a flowchart for optimized fiber placement programming of steered-fiber plies in accordance with one embodiment.

FIG. 9 is a flowchart showing some of the steps executed by the optimized fiber placement programming in accordance with one embodiment. The objective was to develop a method to transform a stream function definition to discrete courses and tows. Ideally the measure of merit for tow add and cut locations is defined such that the location of tow adds and cuts can be optimized. Subsequently, the fiber path and tow mask definitions have to be written in a language that can be used to drive an advanced fiber placement machine.

Referring to FIG. 9, a process for generating optimized fiber placement programming for laying steered-fiber plies in accordance with one embodiment comprises the following processes: a geometry process 22 for creating the geometry of a steered-fiber ply, a tow optimization process 24 for choosing optimum tow cut/add locations, and an output process 26 for outputting G-code for an advanced fiber placement (AFP) machine consistent with the results of the tow optimization. One or more processors can be programmed with respective software modules for geometry creation, tow optimization, and output. The optimization objective, constraints, and G-code output can be tailored to take into account machine-specific parameters (such as number of tows, minimum cut length, and tow width) and user preferences with respect to the penalty function for cutting at a specific radius, the coverage parameter, and balanced cutting (i.e., cutting the same number of tows from each of two neighboring courses as much as possible).

The processes depicted in FIG. 9 are employed to generate the detailed fiber placement definition of a steered-fiber ply with constant thickness. The algorithms of those respective processes will now be described.

1. Geometry

Stream Function:

In the design process disclosed herein, design variables are selected which directly define the stream function (stream function generation algorithm 70). Once the stream function is defined, the thickness distribution and fiber angle distribution are easily computed. The stream function itself can be parameterized straightforwardly, for example, by tensor product polynomial splines. The stream function, assumed to be known, is the starting point for generating the fiber placement details.

Figure 10:
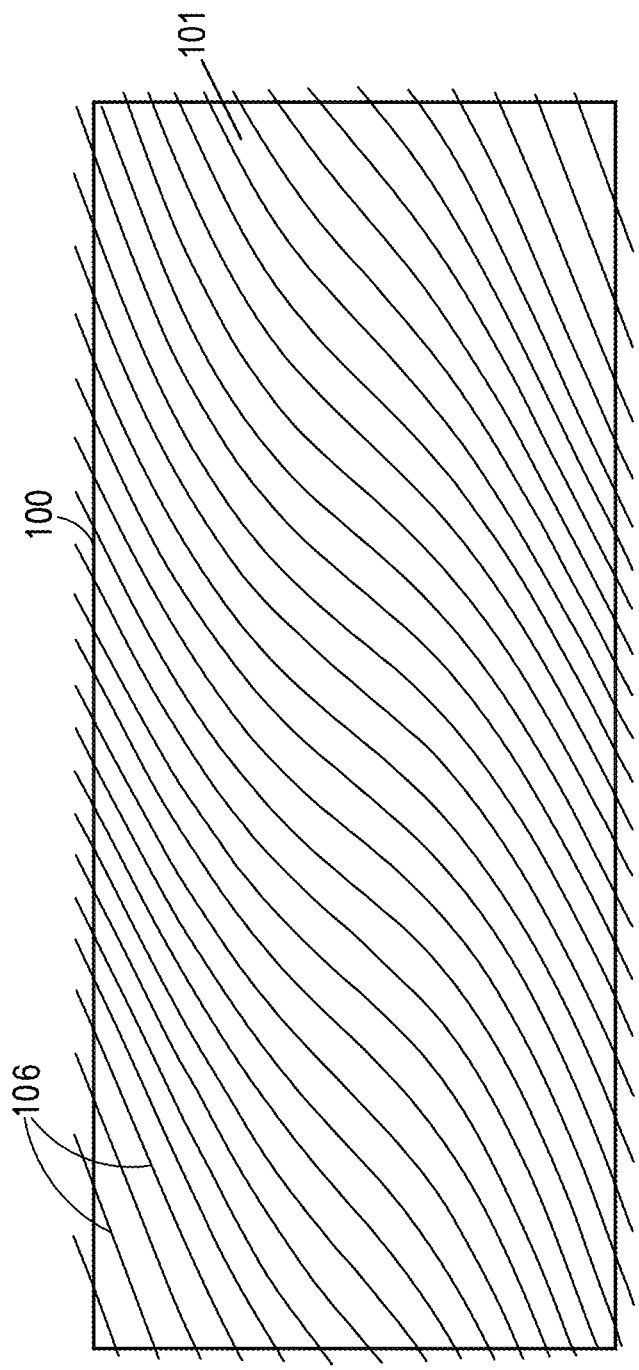
FIG. 10 is a diagram representing stream lines of a stream function superimposed on a domain.
Figure 11:
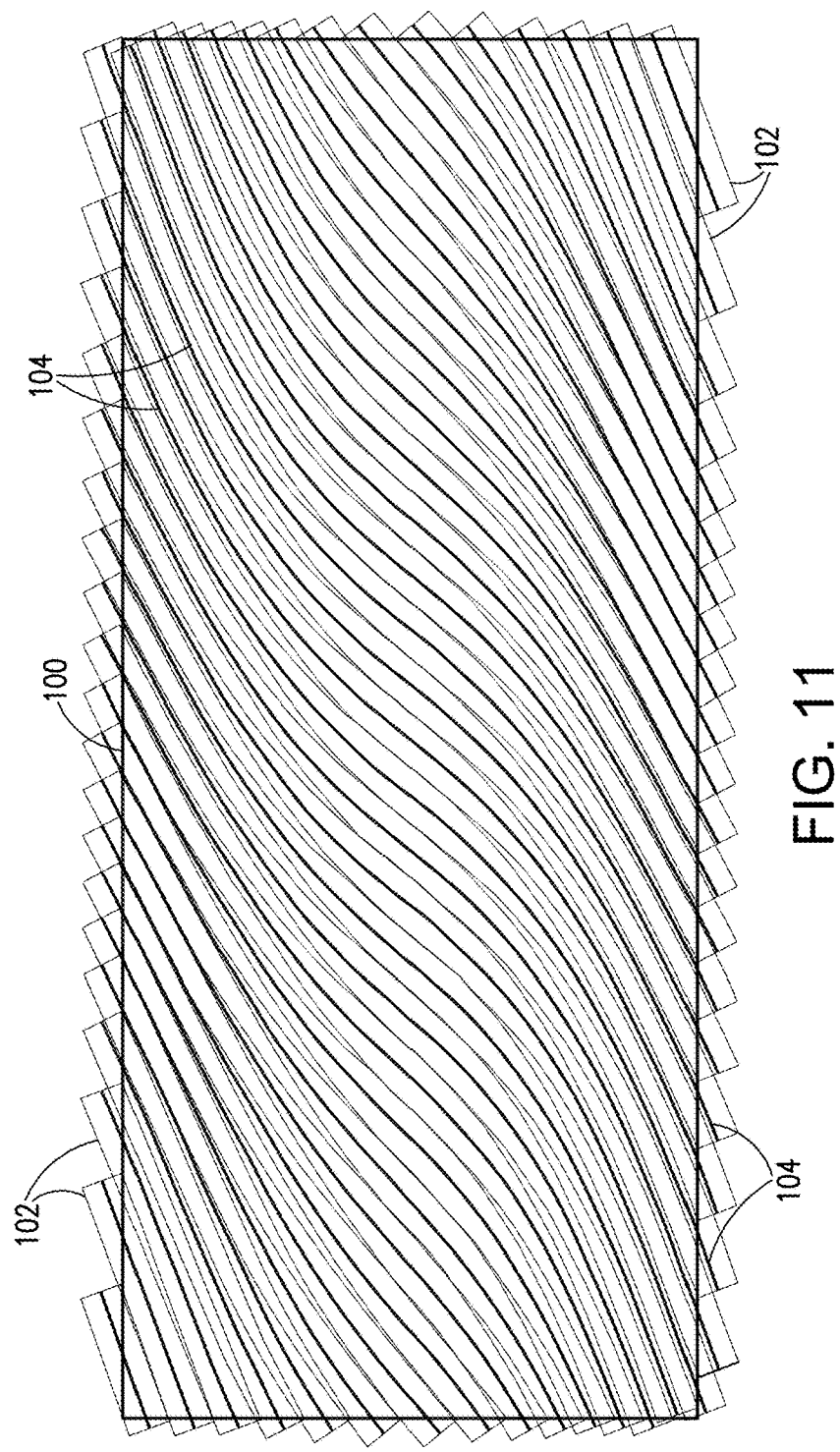
FIG. 11 is a diagram showing a simulation of steered courses overlying a domain (e.g., a panel), trimmed at the domain boundary.

The course centerlines to be implemented in the automated tow placement process correspond to the stream lines generated by the design process depicted in FIG. 3. FIG. 10 shows a multiplicity of stream lines 106 superimposed on a domain 101 with domain boundary 100. FIG. 11 shows a simulation of steered courses 102 overlying the domain 101 that are trimmed at the domain boundary 100. The course centerlines 104 in FIG. 11 correspond to the stream lines 106 in FIG. 10.

Course Pair Generation:

In the next stage of the fiber placement optimization process, the computer system (e.g., a processor) generates pairs of neighboring courses (course pair generation algorithm 72 in FIG. 9). Each pair of neighboring courses is selected such that no gap and minimum overlap exists between the courses. For example, FIG. 12 shows a multiplicity of course centerlines 104 superimposed on domain 101, the two boldfaced curves 104a and 104b representing the centerlines of one pair of neighboring courses.

Figure 12:
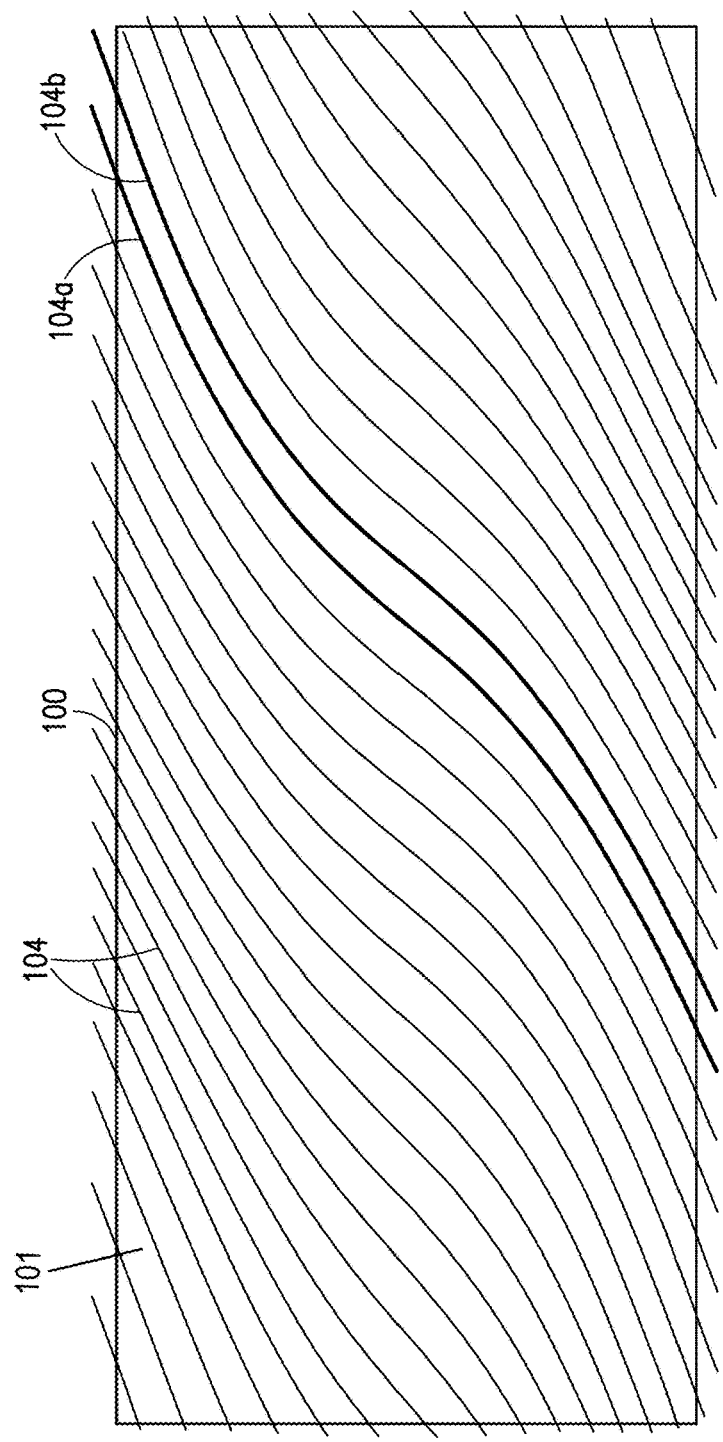
FIG. 12 is a diagram representing a multiplicity of course centerlines superimposed on a domain, the two boldfaced curves representing the centerlines of one pair of neighboring courses.
Figure 13:
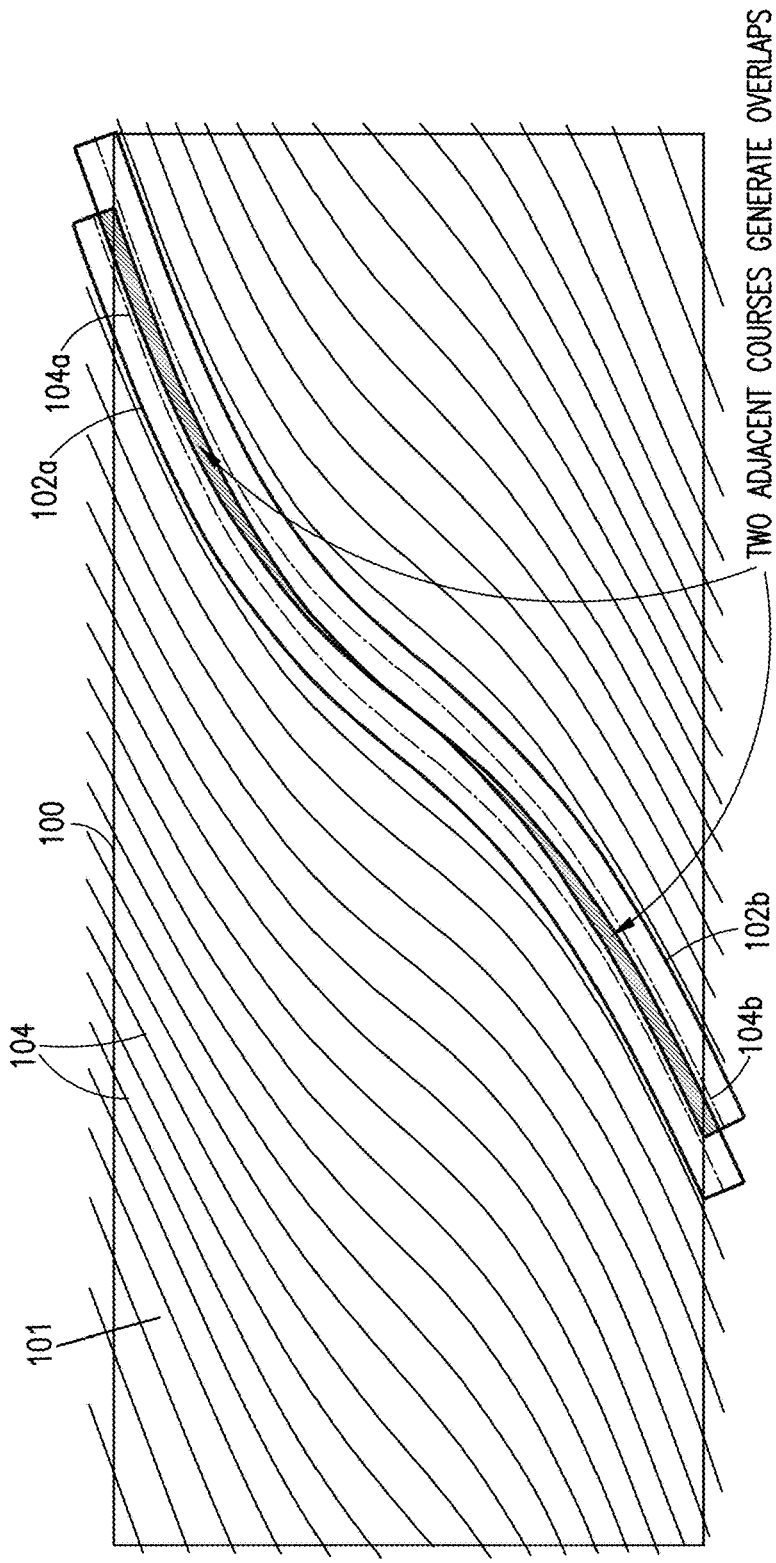
FIG. 13 is a diagram similar to the diagram of FIG. 12, with the addition of representations of two neighboring courses having overlaps (indicated by hatching).
Figure 14:
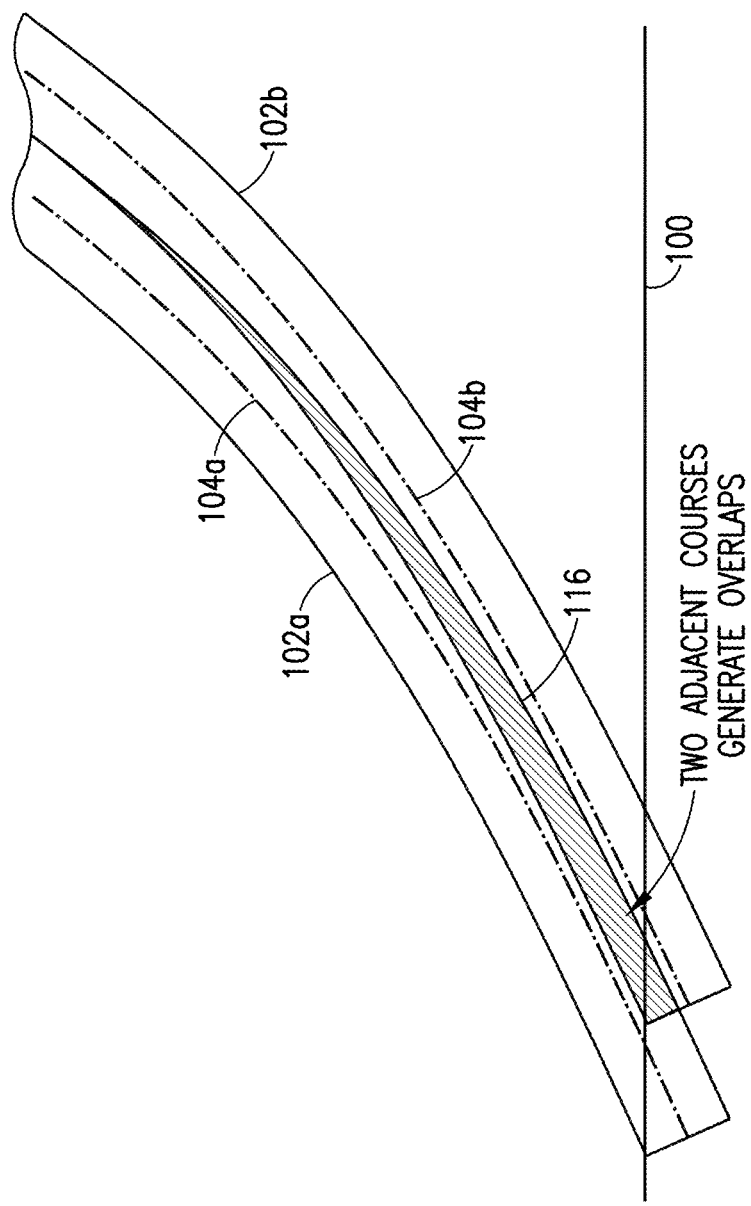
FIG. 14 is a diagram representing (with a magnified scale) respective overlapping portions of the two neighboring courses depicted in FIG. 13.

FIG. 13 differs from FIG. 12 in that the course centerlines 104a and 104b are represented as dash-dot lines instead of boldfaced solid lines and representations of the boundaries of courses 102a and 102b, having centerlines 104a and 104b respectively, have been added. The course boundaries are offsets of the center lines at half the maximum course width. The neighboring courses 102a and 102b have overlaps indicated by hatching in FIG. 13. FIG. 14 shows (with a magnified scale) an overlap 116 formed by respective overlapping portions of the two neighboring courses 102a and 102b depicted in FIG. 13. In the example depicted in FIG. 14, the width of the overlap 116 increases from a point where the boundaries of neighboring courses 102a and 102b intersect toward the respective ends of the courses.

In the example depicted in FIG. 13, none of the course centerlines exit and then re-enter the domain 101. In the event that one or multiple courses completely go outside (including both course boundaries) the domain boundary 100, the course pair generation will take additional steps to take the re-entering courses into account, which process will be described later with reference to FIG. 18.

All Potential Cuts Generated for Overlapped Area:

For each pair of neighboring courses, the computer system (e.g., the same processor which generates course pairs or a different processor that receives generated course pairs from that processor) generates all potential tow cuts for each area of overlap (algorithm 74 in FIG. 9).

Figure 15:
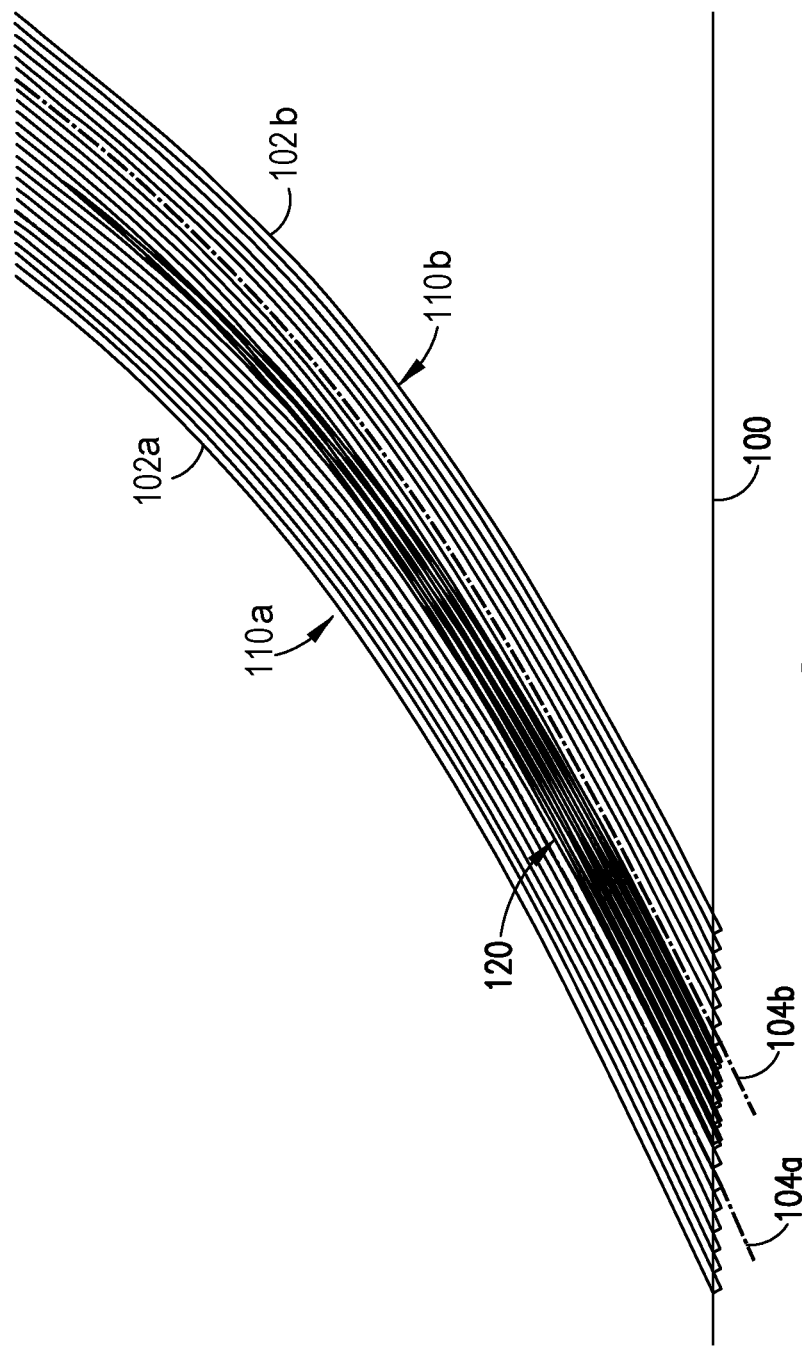
FIG. 15 is a diagram representing portions of tows of two neighboring courses having overlaps.

FIG. 15 is a diagram representing an area of overlap 120 where tows 110a of course 102a overlap with tows 110b of course 102b. The computer system determines where tows 110a in course 102a cross tows 110b in course 102b. Every time two tows cross each other and start overlapping, one of the two tows needs to be cut, or if the overlap ends, the cut tow needs to be added again. The exact location depends on the coverage parameter. In this operation, only "potential" tow cut locations are determined for each tow.

Figure 16:
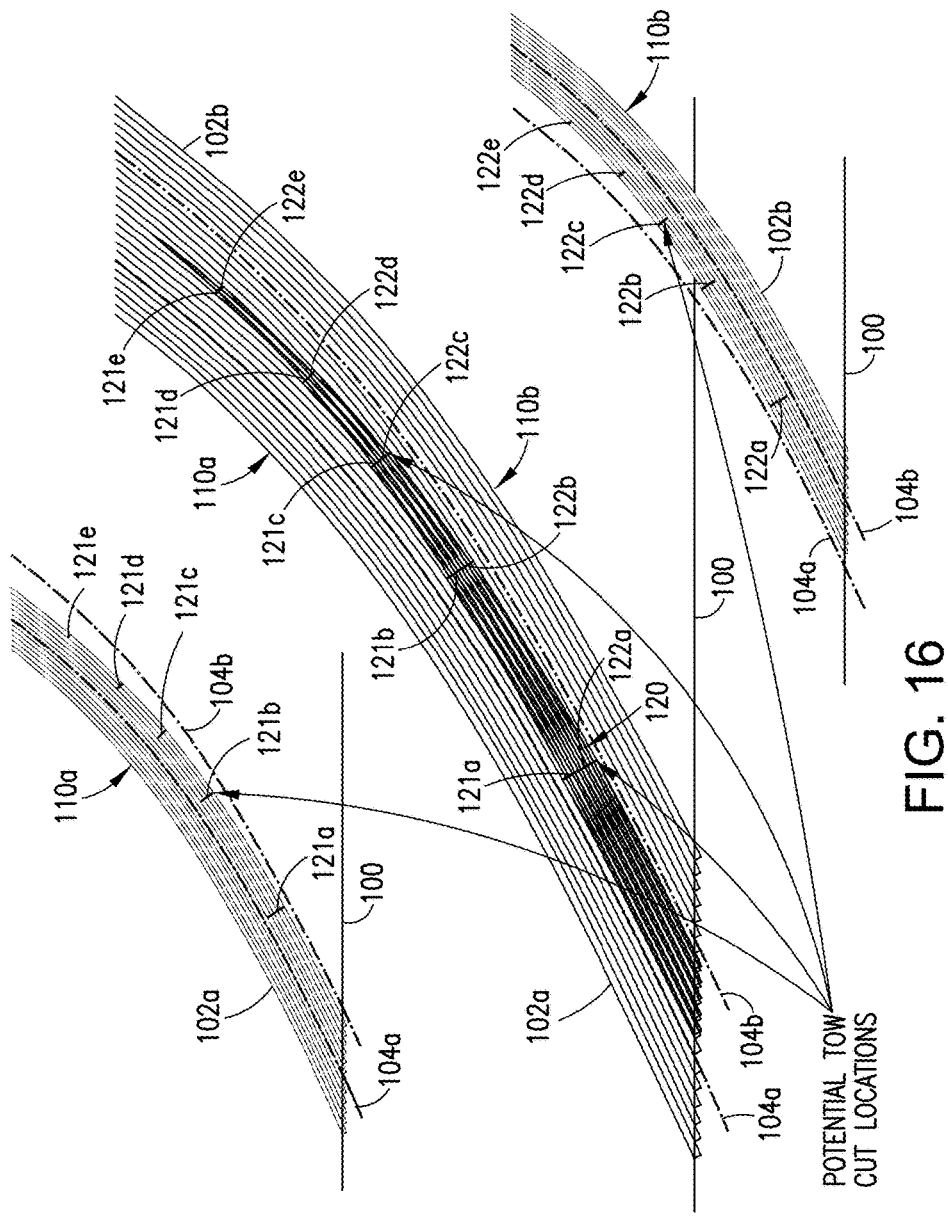
FIG. 16 is a diagram representing portions of tows of two neighboring courses having overlaps, and further including lines indicating potential tow cut locations.

FIG. 16 shows the same area of tow overlap 120 that is depicted in FIG. 15, with the addition of pairs of intersecting short straight lines indicating potential tow cut locations. In the central portion of FIG. 16, an area of overlap 120 is depicted where tows 110a of course 102a overlap with tows 110b of course 102b. A multiplicity of pairs of potential tow cut locations 121a-121e and 122a-122e are indicated by short straight lines generally transverse to the tows 110a and 110b. (Since the course centerlines are not parallel, the cuts of each pair of cuts are also not parallel. Due to the small scale, this aspect is not shown in FIG. 16.) FIG. 16 also shows courses 102a and 102b separated from each other, with the same short straight lines superimposed on each course to indicate the respective sets of potential tow cut locations 121a-121e and 122a-122e. The decision to actually cut or add a tow is made in the tow optimization process 24 (see FIG. 9), taking into account constraints and dependencies as set forth above.

Geometry Information is Generated for Each Potential Cut:

The tow optimization process 24 that determines which tows should be cut/added needs geometry information in a specified format from the geometry process 22. Algorithm 76 (see FIG. 9) generates that geometry information for each potential tow cut. Tows are basically divided in segments that are created by the potential tow cut locations. The following information is passed on for each segment: (a) an index for which course the segment belongs to; (b) an index indicating which tow the segment belongs to; (c) an index indicating which segment in the tow it is; (d) an index indicating the number of the tow of the neighboring course it overlaps with (this index is set to −1 if it does not overlap); (e) an index indicating which overlap region the tow is part of in case the courses overlap more than once (this index is set to −1 if it is not part of an overlap region); (f) the length of the segment; and (g) the centerline curvature values at the minimum cut length distance from the potential tow cut location on each side of the potential tow cut location. (This last information is used to determine the degree of fiber straightening for each of the two potential lay-down directions.)

All of the foregoing information is collected by the computer system and used to generate the following lists: a list of data for each tow that indicates the potential tow cut locations along its length, a list of parameters representing the tow segments, a list of data specifying the lengths of the tow segments, and two lists of data specifying the centerline curvatures at the minimum cut length distance from each potential tow cut location at either side of the potential tow cut location.

2. Tow Optimization

Once the geometry been simulated for each pair of neighboring courses, the tow optimization process 24 can be performed for those same courses without having any knowledge about the actual geometry. This means that the same optimization algorithm can be used for three-dimensional structures as long as the information is in the same format. The tow optimization process 24 (see FIG. 9) comprises the following algorithms:

Two Neighboring Courses:

The tow optimization process 24 executes in a loop over course pairs that are adjacent. The optimization can be done for each pair, where the "penalty" is minimized. The input for the optimization is the geometric information for this pair that is available from the geometry process 22. The computer system retrieves the geometry information for each potential tow cut for each pair of neighboring courses from computer memory (algorithm 78 in FIG. 9).

In accordance with one embodiment, tow optimization is applied to two neighboring courses at a time. This assumes that course centerlines do not intersect and that the amount of course overlap is not extreme. The overlap is characterized by the "thickness build-up", which is a function of the magnitude of the stream function gradient. The structural optimizations performed as part of one project typically constrained the thickness build-up to be less than five or six, which automatically takes care of this problem. The software can be easily modified to accommodate more than two neighboring courses that form an overlap.

Find a Set of Tow Cuts with Minimum Cost:

The optimization of tow cut/add locations is modeled as Mixed Integer Programming and implemented in suitable code, such as C++/CPLEX. The decision to cut/add tows depends on many factors, some more important than others. Some constraints are hard constraints, e.g., constraints caused by machine limitations, while others are dependent on the importance of the constraint, so that the optimizer can select cut location based on preference. These preferences are user-specified input, so that users can prioritize among soft constraints. The overall optimization objective will then be to minimize the total "penalty" of the potential tow cut locations for one set of courses, while satisfying the hard constraints (algorithm 80 in FIG. 9).

In case any of the hard constraints cannot be satisfied, the course pair can be generated using different settings in course pair generation algorithm 72. For example, the amount of overlap between the two courses could be increased a little bit, which might result in a tow segment becoming long enough to meet the minimum cut length constraint. This iteration can be done multiple times until all hard constraints are met, or until the maximum number of iterations is reached, in which case the course pair with the lowest penalty is selected and the user receives an error message indicating that there is a problem. The user is then given a choice to manually solve the problem. In case of the minimum cut length, the user may choose to leave out the short segment or to extend the length to the minimum cut length.

Figure 19:
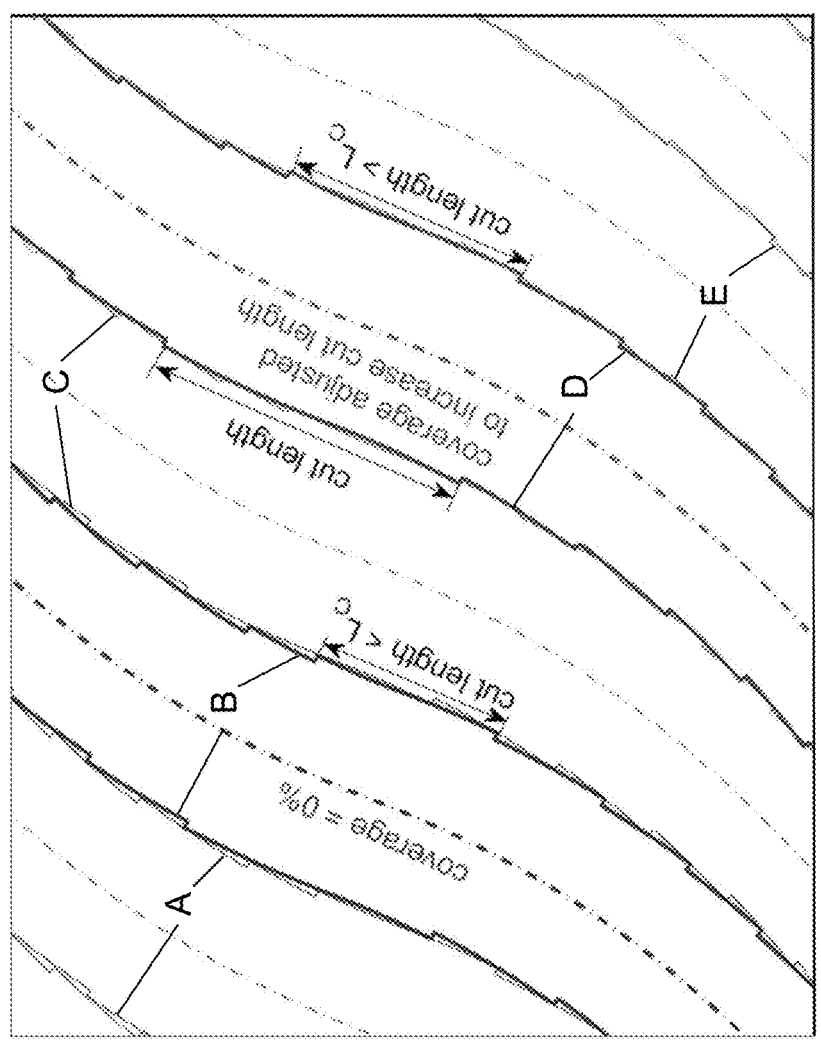
FIG. 19 is a diagram illustrating how changing the coverage parameter can result in increased tow length.

Alternatively, the coverage parameter might be changed and a new set of potential tow cut locations could be generated (algorithm 74 in FIG. 9) to help satisfy the hard constraints in the tow optimization phase 24. For example, FIG. 19 illustrates how changing the coverage parameter can result in increased tow length. The pairs of stepped lines respectively labeled A through E represent the tow cuts along the two course boundaries of respective simulated courses A through E. There is a target coverage parameter chosen, e.g., 50%, that is used to create the tow segments.

However, this value is allowed to change if one of the hard constraints, such as the minimum cut length, is violated in order to find a feasible solution. The term "cut length" is the length of the tow segment; $L_C$ is the minimum cut length. The cut length should be greater than $L_C$. In this example the course centerlines of courses A through E are exactly the same, shifted with respect to each other. The tows in course B are generated assuming a coverage parameter of 0%, and the piece indicated with "cut length<$L_C$" is too short. The tows in course D are generated assuming a coverage parameter of 50%, making that tow segment at the bottom longer than the minimum cut length, thus satisfying a hard constraint. The difference in coverage can be seen in how far the tows overlap the tows of the neighboring course, as previously illustrated in FIGS. 6A-6C.

Some of the logic/decision variables used in the tow optimization are:

The relation between cut variables and segment variables: Y=|X1−X2|. Each tow has a list that represents the segments (X), and the "act of cutting/adding" (Y). X=1 if the tow segment is active; X=0 if it is inactive (i.e., not placed). Adding or cutting tows is represented by Y=1, while Y=0 when the status of the tow is unchanged at a potential tow cut location. So if a tow goes from active to inactive, the logic Y=|X1−X2| is represented by: 1=|1−0|.

Minimum length constraint.

Maximum cut constraint: at each overlap, a tow can be change status at most twice (to avoid small segments on-and-off).

Overlap constraint: when there is an overlap, only one segment can be active.

Non-overlap constraint: when a segment is not an overlap, it has to be active.

Minimum distance between segments.

If a tow is not cut, none of the tows closer to the centerline should be cut either (i.e., all of them should be active).

If the path curvature is larger than a certain value, cutting tows on the large radius should be avoided as much as possible to avoid fiber straightening (example of a desirable constraint).

The optimizer generates a list of "segment variables" for each tow, indicating whether it is active (1) or inactive (0), and a list of "cut variables", indicating whether a tow is cut/added at the potential tow cut location (1) or if the status is unchanged (0).

The code is set up to automatically generate the tow cut information for a full ply.

3. Output

Visualization:

After the tow cut/add locations have been optimized, the segment variables for all courses are used to display the active tow segments. The final design can be displayed on a display device such as a computer monitor or other display screen. More specifically, the display device displays a visual representation of a steered-fiber ply comprising a multiplicity of courses, each course comprising a respective multiplicity of tows including tow cuts for neighboring courses with overlaps that conform to a coverage parameter constraint.

Figure 17:
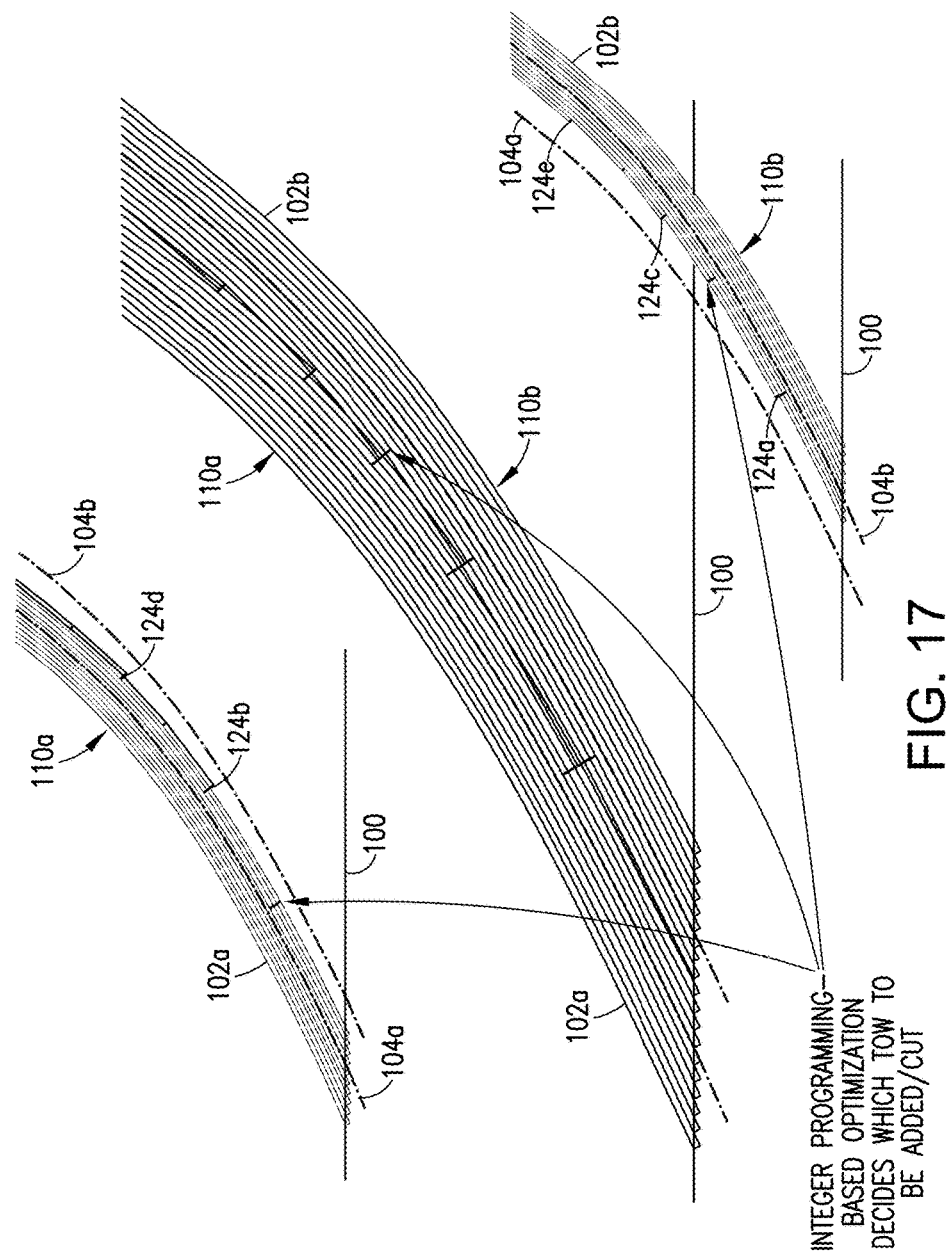
FIG. 17 is a diagram representing portions of tows of two neighboring courses after the optimization process disclosed herein has decided which tows to cut and the locations at which to cut these tows to reduce overlap.

A visualization of optimized tow cuts/adds for two neighboring courses 102*a* and 102*b* is shown in FIG. 17. The overlap 120 seen in FIG. 16 has been reduced in the visualization of FIG. 17 by cutting tows so that their overlap conforms to a coverage parameter constraint. In the example depicted in FIG. 17, two of tows 110*a* have been cut at cut locations 124*b* and 124*d* along the outside of course 102*a*, while three of tows 110*b* have been cut at cut locations 124*a*, 124*c* and 124*e* along the inside of course 102*b*.

G-Code:

The segment and cut variables are combined with centerline coordinates and direction vectors to generate G-code that can be used to drive the advanced fiber placement machine. The result will be a steered-fiber ply having an optimized structure that satisfies constraints on strength, curvature and thickness.

Optionally, the course pair generation algorithm 72 of the optimization process depicted in FIG. 9 takes into account re-entering course centerlines. Prior to course pair generation, the stream function generation algorithm 70 generates all stream lines on an extrapolated version of the domain (e.g., extrapolated by slightly more than one course width) without taking into account which stream lines exit and then re-enter the domain boundary and which stream lines are disposed completely within the domain boundary. The course pair generation algorithm 72 then identifies which course centerlines (i.e., corresponding to the stream lines) go completely outside the domain boundary (including both course boundaries). Those then get split up in two (or more) pieces. Since initially spacing between stream lines is based on "no gap/minimum overlap" between courses, the pieces that fall inside the domain might have too much overlap. The course pair generation algorithm 72 will then pick different stream function values to create the centerlines for the new "segmented" courses, which can be different for each piece, because now they are no longer one, continuous course. All course centerlines between the new courses and the domain boundaries then have to be determined again, based on the no gap/minimum overlap algorithm. These new course centerlines are thereafter incorporated into the AFP machine programming.

Figure 18:
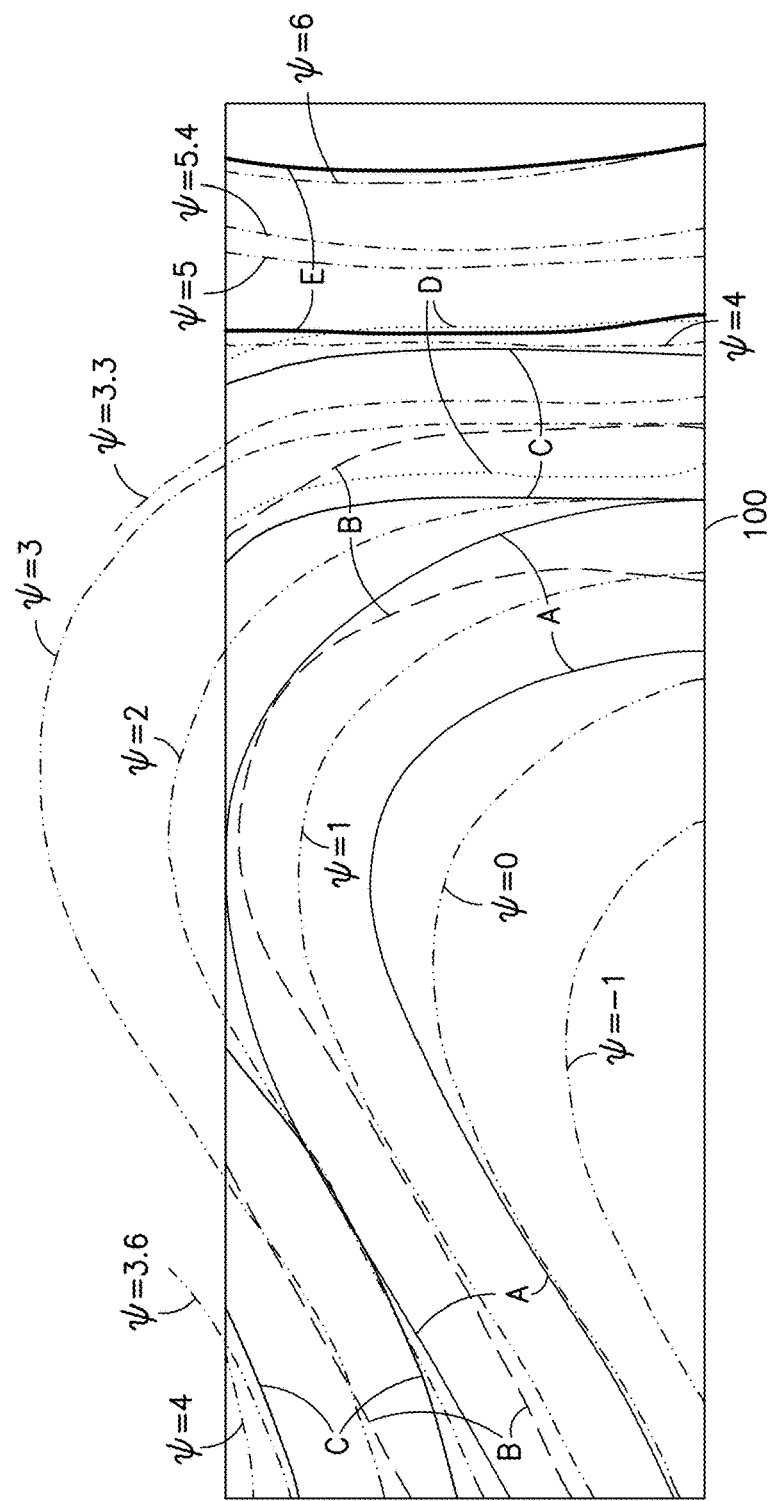
FIG. 18 is a diagram representing the generation of alternative stream lines taking into account courses which exit and then re-enter a domain boundary.

FIG. 18 is a diagram representing the generation of alternative stream lines, taking into account course centerlines which exit and then re-enter a domain boundary 100. Each stream line (indicated by a chain of alternating dashes and paired dots in FIG. 18) has a respective stream function value $\psi$, e.g., $\psi=-1$, $\psi=0$, $\psi=1$, $\psi=2$, etc. The stream function values equal to whole integers represent the initial set of streamlines generated by stream function generation algorithm 70. The stream lines for $\psi=3.6$ and $\psi=5.4$ (see FIG. 18) represent the results of the recalculation of the stream lines taking into account the initially computed re-entering centerlines for courses which overlap too much with a neighboring course.

Before explaining the significance of FIG. 18 in more detail, clarification of the symbology therein is called for. As previously noted, the curved lines made up of alternating dashes and dot pairs represent respective streamlines. The pair of solid curved lines labeled A represent the two course boundaries of a simulated course A whose centerline corresponds to stream line $\psi=1$, which course boundaries are completely inside the domain boundary 100. The three dashed curved lines labeled B represent portions of the two course boundaries of a simulated course B whose centerline corresponds to stream line $\psi=2$. The inner boundary of course B lies completely inside the domain boundary 100, but the outer boundary of course B has two segments disposed inside the domain boundary 100 and one segment (not shown) disposed outside the domain boundary 100. The two pairs of solid curved lines labeled C represent portions of two course boundaries of a simulated course C whose centerline corresponds to stream line $\psi=3$, which boundaries of course C each have a respective portion (not shown) disposed outside the domain boundary 100. In other words, the course C exits the domain boundary 100 completely and then re-enters the domain boundary 100.

Because simulated course C goes completely outside the domain boundary 100, the course pair generation algorithm will take this re-entering course into account. More specifically, the following steps are performed when one course of a pair of neighboring courses completely exits and then re-enters a specified domain: (1) determine an amount of overlap within the specified domain between the pair of neighboring courses; (2) select two course pieces within the specified domain which overlap the other course of the pair of neighboring courses less degree than the one course does when the amount of overlap within the specified domain between the pair of neighboring courses is greater than a specified threshold; and (3) substituting new course data representing the selected two course pieces in place of course data representing the one course of the pair of neighboring courses.

In the example shown in FIG. 18, the course A having a centerline corresponding to stream function value $\psi=1$ is completely inside the domain boundary 100, which state does not require any adjustment to that course centerline. The course B has a centerline corresponding to $\psi=2$ which exits and then re-enters the domain boundary 100, but one boundary of course B is completely inside the domain boundary 100, which is again not a problem. The course C has a centerline corresponding to $\psi=3$ which exits and then re-enters the domain boundary 100, but both boundaries of course C are completely outside the domain boundary 100. Spacing with respect to course C is dominated by the distance outside the domain boundary 100. Within the domain, simulated course C overlaps too much with course B. The solution is to split up course C. Different $\psi$ values are selected for each piece so one boundary of the new simulated course touches the neighboring boundary of course B with and does not cause a gap. In the example shown in FIG. 18, a new left course piece (not shown in FIG. 18) having a centerline corresponding to $\psi=3.6$ was selected, while a new right course piece D (the boundaries of which are indicated by a pair of dotted lines in FIG. 18) has a centerline at $\psi=3.3$. The centerlines corresponding to $\psi=4$ and $\psi=5$ are based on the old spacing. In this example, a new stream function value $\psi$ was selected such that a new course E will have a boundary that touches the closest boundary of course D. In this case a stream function value of $\psi=5.4$ was chosen and the stream function value $\psi=5$ was discarded.

Since the optimization described above does not rely on the geometry of the problem, it can be easily extended to three-dimensional problems as long as all the inputs can be calculated. By allowing users to specify preference by setting a penalty function for soft constraints, this program provides flexibility for users who can easily modify the program based on specific problems. User-specified hard constraints, i.e., certain tow segments have to be taped, can be easily added to the problem. Solving each problem (a pair of neighboring courses) takes less than one second. Although overall computational time is very low, the preliminary results show that the most time-consuming portion of the program is to generate the geometric information of the problem.

The design variables in the process disclosed herein design an individual ply, or by extension a balanced pair. More variables can be added to design more plies in a similar manner. However, the structural analysis upon which the optimization/design process depends only makes sense for the laminate in toto, and so while the design is defined in terms of plies, the design process itself works on a laminate.

As is well known, a composite panel may be constructed with multiple (e.g., twenty) plies. For a conventional ply on a flat panel, each ply has fiber paths which are described entirely by ply angles selected from the group consisting of 0°, ±45° and 90°. One exemplary steered-fiber composite panel may have four steered plies, with the other plies being of the conventional variety. For example, pairs of 0° plies or ±45° plies in a conventional panel may be replaced with pairs of steered-fiber plies, the plies of each pair being balanced. The steered-fiber plies of each pair may be separated by one or more intervening conventional plies. This proposed laminate structure is merely exemplary.

The technology described above is not only applicable to steering fibers to tailor laminate stiffness, but also to areas where fiber steering is required to maintain a certain fiber angle/rosette. The geometric parameters can be generated on either a flat or curved surface. The optimization module does not need any information about the geometry, but uses tow length and curvature information that is passed on from the geometry module, as well as information about which other tows and courses are overlapping. The example described in detail above employed an algorithm for two courses, but the process described herein can also be done if more than two courses overlap each other.

Figure 20:
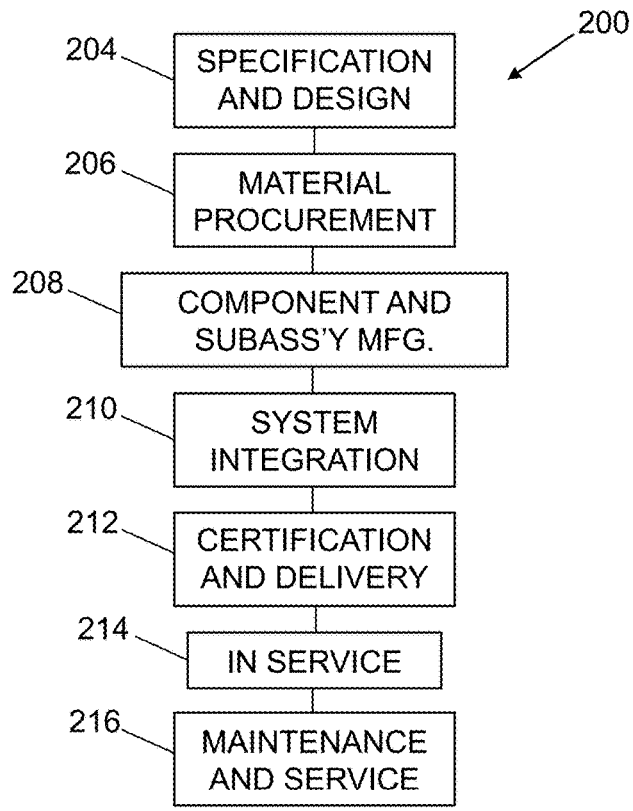
FIG. 20 is a flow diagram of an aircraft production and service methodology.
Figure 21:
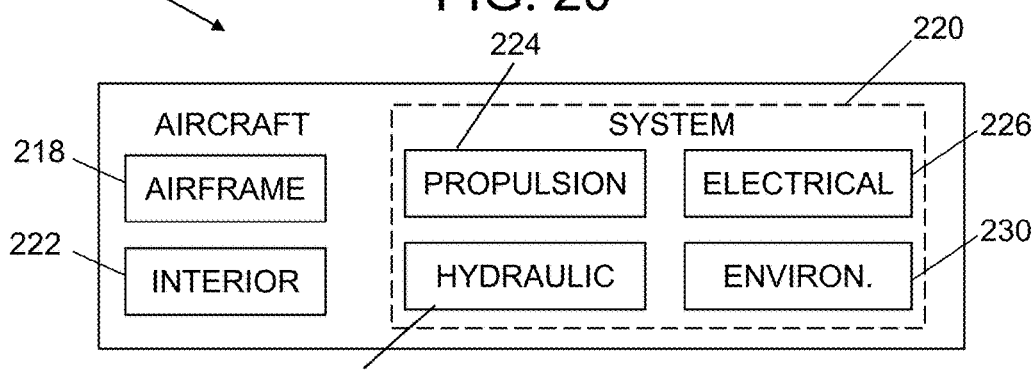
FIG. 21 is a block diagram showing systems of an aircraft.

The system and methods disclosed above may be employed in an aircraft manufacturing and service method 200 as shown in FIG. 20 for fabricating components of an aircraft 202 of a type depicted in FIG. 21. During pre-production, exemplary method 200 may include specification and design 204 of the aircraft 202 and material procurement 206. During production, component and subassembly manufacturing 208 and system integration 210 of the aircraft 202 takes place. Thereafter, the aircraft 202 may go through certification and delivery 212 in order to be placed in service 214. While in service by a customer, the aircraft 202 is scheduled for routine maintenance and service 216 (which may also include modification, reconfiguration, refurbishment, and so on).

Each of the processes of method 200 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 21, the aircraft 202 produced by exemplary method 200 may include an airframe 218 (comprising, e.g., a fuselage, frames, stiffeners, wing boxes, etc.) with a plurality of systems 220 and an interior 222. Examples of high-level systems 220 include one or more of the following: a propulsion system 224, an electrical system 226, a hydraulic system 228, and an environmental control system 230. Any number of other systems may be included. Although an aerospace example is shown, the principles disclosed herein may be applied to other industries.

Apparatus and methods embodied herein may be employed during one or more of the stages of the production and service method 200. For example, components may be fabricated during production process 208 using the optimized fiber placement techniques disclosed herein. Also, one or more apparatus embodiments, method embodiments, or a combination thereof may be utilized during the production stages 208 and 210, for example, by substantially expediting assembly of or reducing the cost of an aircraft 202.

While the invention has been described with reference to various embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices having a processing unit (e.g., a central processing unit) and some form of memory (i.e., computer-readable medium) for storing a program which is readable by the processing unit.

The method claims set forth hereinafter should not be construed to require that the steps recited therein be performed in alphabetical order (alphabetical ordering in the claims is used solely for the purpose of referencing previously recited steps) or in the order in which they are recited. Nor should they be construed to exclude two or more steps or portions thereof being performed concurrently or to exclude any portions of two or more steps being performed alternatingly.

The invention claimed is:

1. A method, performed by a computer system, for determining optimum tow cut locations for steered-fiber placement, said method comprising:
   (a) generating stream function data with a multiplicity of corresponding stream lines;
   (b) generating course pair data representing successive pairs of neighboring courses having centerlines corresponding to the stream lines representing the stream function data generated in operation (a) such that there is no gap between the neighboring courses; and
   for each pair of neighboring courses:
   (c) determining potential tow cut locations where any uncut tow from one of the pair of neighboring courses will potentially overlap with any uncut tow from the other of the pair of neighboring courses in dependence on a set of allowable coverage parameter values,
   (d) generating geometry data for each potential tow cut location, and
   (e) selecting which tows of the pair of neighboring courses should be cut or added at which tow cut locations selected from the potential tow cut locations determined in operation (c) and in which direction the courses should be laid down, wherein the tows selected for cutting at the selected tow cut locations and the selected direction for course laydown minimize a penalty function taking a plurality of constraints into account;
   (f) generating machine code for controlling a fiber placement machine to cut the tows selected for cutting in operation (e) and lay down the courses in the direction selected in operation (e);
   (g) storing the machine code generated in operation (f) on a computer-readable medium; and
   (h) operating a computer numerical control tow placement machine in accordance with the machine code stored on said computer-readable medium,
   wherein said plurality of constraints comprise a maximum thickness build-up, a minimum turning radius for a centerline of each neighboring course, a coverage parameter which determines where tows will be terminated and restarted with respect to a boundary, a minimum cut length for each tow, and a maximum number of tow cuts within an overlap area, and
   wherein operation (e) further comprises generating a list of segment variables for each tow, indicating whether it is active or inactive, and generating a list of cut variables, indicating whether a tow is cut or added at a potential tow cut location or if the status is unchanged.

2. The method as recited in claim 1, wherein operation (d) comprises generating the following: a list of data for each tow that indicates the potential tow cut locations along a length, a list of parameters representing the tow segments, a list of data specifying respective lengths of the tow segments, and two lists of data specifying a centerline curvature at a minimum cut length distance from each potential tow cut location at either side of the potential tow cut location.

3. The method as recited in claim 1, further comprising displaying a visual representation of a steered-fiber ply comprising a multiplicity of courses, each course comprising a respective multiplicity of tows, including tows selected for cutting in operation (e) with overlaps that conform to a coverage parameter constraint.

4. The method as recited in claim 1, wherein said plurality of constraints comprise an overlap constraint, according to which only one segment can be active when there is an overlap, and a non-overlap constraint, according to which a segment is active when there is no overlap.

5. The method as recited in claim 1, wherein operation (e) takes the following constraint into account: none of the tows between the two outermost tows that are not cut should be cut.

6. The method as recited in claim 1, wherein operation (e) takes the following constraint into account: if a curvature of a path of a course is larger than a specified threshold, the tows along an outer radius of the course are not cut to avoid fiber straightening, depending on the direction in which the course is being laid down.

7. The method as recited in claim 1, wherein operation (b) further comprises the following steps performed when one course of a pair of neighboring courses completely exits and then re-enters a specified ply domain:
   replacing the re-entering course by multiple courses by splitting up the re-entering course at the domain boundary; and
   for each newly created course:
   determining the overlap between the new course and the neighboring course;
   adjusting the position of the new course to reduce the amount of overlap below a certain threshold if the amount of overlap is larger than this threshold; and
   generating course data for the newly created courses and original neighboring course.

8. The method as recited in claim 2, further comprising displaying a visual representation of a steered-fiber ply comprising a multiplicity of courses, each course comprising a respective multiplicity of tows, including tows selected for cutting in operation (e) with overlaps that conform to a coverage parameter constraint.

9. The method as recited in claim 4, further comprising displaying a visual representation of a steered-fiber ply comprising a multiplicity of courses, each course comprising a respective multiplicity of tows, including tows selected for cutting in operation (e) with overlaps that conform to a coverage parameter constraint.

10. The method as recited in claim 5, further comprising displaying a visual representation of a steered-fiber ply comprising a multiplicity of courses, each course comprising a respective multiplicity of tows, including tows selected for cutting in operation (e) with overlaps that conform to a coverage parameter constraint.

11. The method as recited in claim 6, further comprising displaying a visual representation of a steered-fiber ply comprising a multiplicity of courses, each course comprising a respective multiplicity of tows, including tows selected for cutting in operation (e) with overlaps that conform to a coverage parameter constraint.

12. The method as recited in claim 7, further comprising displaying a visual representation of a steered-fiber ply comprising a multiplicity of courses, each course comprising a respective multiplicity of tows, including tows selected for cutting in operation (e) with overlaps that conform to a coverage parameter constraint.

13. A method for laying a composite ply comprising steered fibers, said method comprising:
(a) generating stream function data with a multiplicity of corresponding stream lines;
(b) generating course pair data representing successive pairs of neighboring courses having centerlines corresponding to the stream lines representing the stream function data generated in operation (a) such that there is no gap between the neighboring courses; and
for each pair of neighboring courses:
(c) determining potential tow cut locations and add locations where any uncut tow from one of the pair of neighboring courses will potentially overlap with any uncut tow from the other of the pair of neighboring courses in dependence on a set of allowable coverage parameter values,
(d) generating geometry data for each potential tow cut location;
(e) selecting tow cut and add locations from the potential tow cut locations determined in operation (c) which result in minimizing a value of a penalty function for simulated placement of tows for one set of courses, taking into account a plurality of constraints;
(f) generating machine code for controlling a fiber placement machine to lay down courses and to cut and add tows at the selected tow cut and add locations; and
(g) automatically laying down courses and cutting and adding tows in accordance with said machine code,
wherein said plurality of constraints comprise a maximum thickness build-up, a minimum turning radius for a centerline of each neighboring course, a coverage parameter which determines where tows will be terminated and restarted with respect to a boundary, a minimum cut length for each tow, and a maximum number of tow cuts within an overlap area, and steps (a) through (f) are performed by processors, and
wherein operation (d) comprises generating the following: a list of data for each tow that indicates the potential tow cut locations along its length, a list of parameters representing the tow segments, a list of data specifying the lengths of the tow segments, and two lists of data specifying the centerline curvature at the minimum cut length distance from the tow cut locations at either side of the potential tow cut location.

14. The method as recited in claim 13, further comprising displaying a visual representation of a steered-fiber ply comprising a multiplicity of courses, each course comprising a respective multiplicity of tows, including tow cuts for neighboring courses with overlaps that conform to a coverage parameter constraint.

15. The method as recited in claim 13, wherein said plurality of constraints comprise an overlap constraint, according to which only one tow segment can be active when there is an overlap, and a non-overlap constraint, according to which a tow segment is active when there is no overlap.

16. The method as recited in claim 13, wherein operation (e) takes the following constraint into account: none of the tows between the two outermost tows that are not cut should be cut.

17. The method as recited in claim 13, wherein operation (e) takes the following constraint into account: if a curvature of a path of a course is larger than a specified threshold, the tows along an outer radius of the course are not cut to avoid fiber straightening, depending on the direction in which the course is being laid down.

18. The method as recited in claim 16, further comprising displaying a visual representation of a steered-fiber ply comprising a multiplicity of courses, each course comprising a respective multiplicity of tows, including tow cuts for neighboring courses with overlaps that conform to a coverage parameter constraint.

19. The method as recited in claim 17, further comprising displaying a visual representation of a steered-fiber ply comprising a multiplicity of courses, each course comprising a respective multiplicity of tows, including tow cuts for neighboring courses with overlaps that conform to a coverage parameter constraint.

20. A system for designing a steered-fiber ply, comprising one or more processors programmed to execute the following operations:
(a) generating stream function data with a multiplicity of corresponding stream lines;
(b) generating course pair data representing successive pairs of neighboring courses having centerlines corresponding to the stream lines representing the stream function data generated in operation (a) such that there is no gap between the courses; and
for each pair of neighboring courses:
(c) determining potential tow cut locations and add locations where any uncut tow from one of the pair of neighboring courses will potentially overlap with any uncut tow from the other of the pair of neighboring courses in dependence on a set of allowable coverage parameter values,
(d) generating geometry data for each potential tow cut location; and
(e) selecting tow cut and add locations from the potential tow cut locations determined in operation (c) which result in minimizing a value of a penalty function for simulated placement of tows for one set of courses, taking into account a plurality of constraints, and
(f) generating machine code for controlling a fiber placement machine to cut the tows selected for cutting in operation (e) and lay down the courses in the direction selected in operation (e);
(g) storing the machine code generated in operation (f) on a computer-readable medium;

(h) controlling a computer numerical control tow placement machine to operate in accordance with the machine code stored on said computer-readable medium; and
(i) displaying a visual representation of a steered-fiber ply comprising a multiplicity of courses, each course comprising a respective multiplicity of tows, including tows cut or added at said selected tow cut and add locations,
wherein said plurality of constraints comprise a maximum thickness build-up, a minimum turning radius for a centerline of each neighboring course, a coverage parameter which determines where tows will be terminated and restarted with respect to a boundary, a minimum cut length for each tow, and a maximum number of tow cuts within an overlap area, and
wherein operation (d) comprises generating the following: a list of data for each tow that indicates the potential tow cut locations along its length, a list of parameters representing the tow segments, a list of data specifying the lengths of the tow segments, and two lists of data specifying the centerline curvature at the minimum cut length distance from the tow cut locations at either side of the potential tow cut location.

21. The system as recited in claim 20, further comprising a display device, wherein one of said processors is programmed to control said display device to display a visual representation of a steered-fiber ply comprising a multiplicity of courses, each course comprising a respective multiplicity of tows, including tows selected for cutting in operation (e) with overlaps that conform to a coverage parameter constraint.

* * * * *